United States Patent [19]
Sarhan et al.

[11] Patent Number: 5,731,419
[45] Date of Patent: Mar. 24, 1998

[54] FREEZING TOLERANCE PROTEINS WCS19 AND WCOR410 FROM GRAMINEAE

[75] Inventors: Fathey Sarhan; Mario Houde; Jean-Francois Laliberte, all of Quebec, Canada

[73] Assignee: Universite du Quebec a Montreal, Montreal, Canada

[21] Appl. No.: 106,981

[22] Filed: Aug. 16, 1993

[51] Int. Cl.$^6$ .................... C07K 14/415; C12N 15/29
[52] U.S. Cl. ................ 530/375; 530/370; 435/69.1; 435/252.3; 435/320.1; 536/22.1; 536/23.1; 536/23.6
[58] Field of Search ................ 435/69.1, 252.3, 435/320.1; 530/375, 370; 536/22.1, 23.1, 23.6

[56] References Cited

PUBLICATIONS

Guo et al, "Characterization of a Cold-Regulated Wheat Gene Related to Arabidopsis cor47", Plant Physiol. 100:915–922 (1992).
Gulick et al, "Stress-Induced Gene ESI35 from Lophopyrum elongatum", Plant Physiol. 103:1031–1032 (1993).
Danyluk et al, "Differential expression of gene encoding an acidic dehydrin in chilling sensitive and freezing tolerant gramineae species", FEBS Letters 344:20–24 (1994).
Houde et al., *Plant Physiol.* (1992) 99, pp. 1381–1387 Aug., 1992.
Houde et al. *Mol. Gen. Genet.* (1992) 234:43–48 Jul., 1992.
Danyluk et al. *Plant Cell Physiol.* (1990) 31 (5) pp. 609–619.
Perras et al. *Plant Physiol.* (1989) 89, pp. 577–585.
Glover *Gene Cloning* (1984) pp. 1–19.
Lerner *Nature* (1982) 299:592–596.

*Primary Examiner*—Vasu S. Jagannathan
*Assistant Examiner*—Elizabeth C. Kemmerer
*Attorney, Agent, or Firm*—Nixon & Vanderhye P.C.

[57] ABSTRACT

The present invention relates to three novel genes which have been isolated from cold-tolerant wheat species and which are induced by low temperature. The first gene, Wcs19, is preferentially expressed in green leaf tissues of tolerant gramineae species and requires both light and low temperature for maximal induction. The second gene, Wcs120, is induced only by low temperature. Different from the protein encoded by Wcs19, the protein encoded by Wcs120 contains two repeated domains that are highly conserved among RAB (rice abscisic acid-induced) and dehydrin families and appears to be light-independent. The Wcs120 protein does not however contain a serine-rich sequence present in RAB and dehydrin families. Finally, the present invention also relates to a third gene, Wcor410, also induced by low temperature as well as water stress and, to a lesser extend, by ABA. Its expression is light-independent. The protein encoded by this gene contains a serine-rich stretch as found in several drought induced proteins.

2 Claims, 18 Drawing Sheets

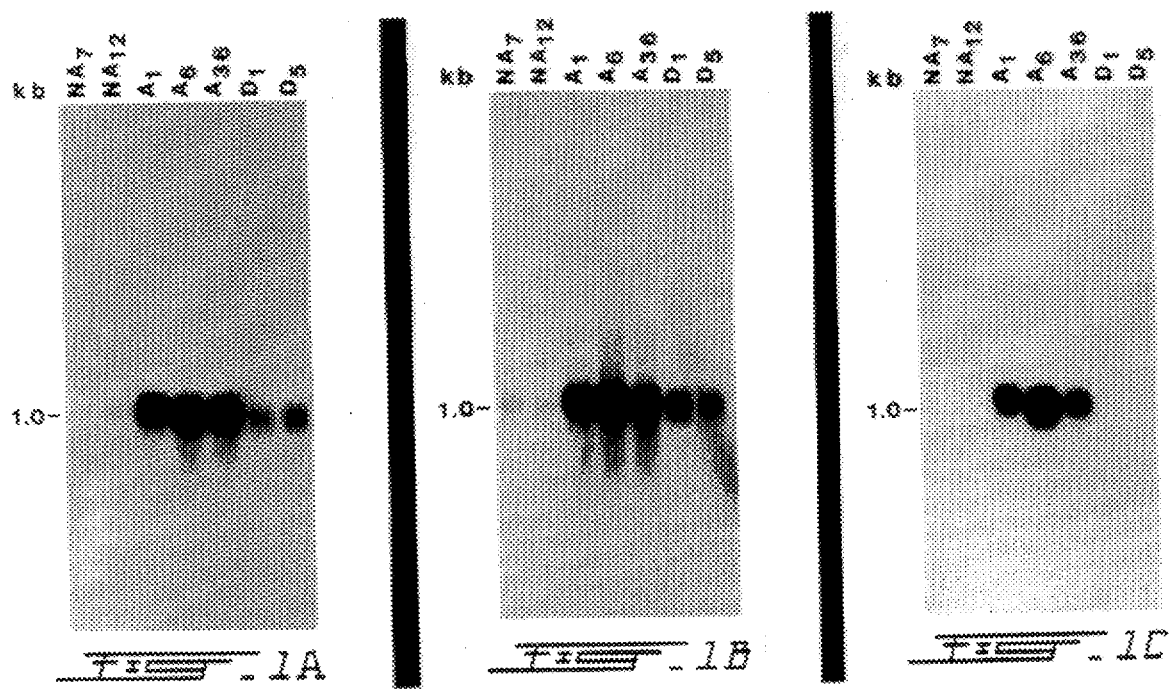

```
  1       tttttttttgcgaccaaaatgaacaagtaaatttactccctcacaagc
 49.      atatgcaaatatattccaccaagaatattagtcggtcctcgctatcaa
 97       ccacatctaaaaccatgtcaacgaatggaaacaacaccaccttaaaag
145       tatccacacgagaaggctccttatatttgtattaacagaagagcaaaa
193       agatatagctgtatgatttcagcgatccaaatccgcatggtgcagcga
 (1)                M  I  S  A  I  Q  I  R  M  V  Q  R
                    α  α  α  α  α  α  α  α  α  α  α  α
241       tgcgcaagactaccatttccaatcggcacacatcctgtctccttccac
(13)       C  A  R  L  P  F  P  I  G  T  H  P  V  S  F  H
           α  ⌐  ⌐  ʊ  ⌐  ʊ  β  β  ʊ  ʊ  ʊ  β  β  β  β  β
289       aacctaccctacccacccatccatcagcagttttctatcgaccaatg
(29)       N  L  P  Y  P  P  T  H  Q  Q  F  F  Y  R  P  M
           ʊ  ʊ  ⌐  ʊ  ʊ  ʊ  ʊ  ʊ  β  β  β  β  β  ʊ  α  ⌐
337       gcttcttcttccgtgctgctcggagcctcggccacggccgcgctcacc
(45)       A  S  S  S  V  L  G  A  S  A  T  A  A  L  T
           ⌐  ⌐  ⌐  β  β  β  β  β  α  α  α  β  β  β  β  β
385       ggcaccccggcaggcaaggcccttccccggccttgcttcctcgccgct
(61)       G  T  P  A  G  K  A  L  P  R  P  C  F  L  A  A
           ʊ  ʊ  ʊ  ʊ  ʊ  ʊ  ʊ  ʊ  ʊ  ʊ  ʊ  ⌐  α  α  α  α  α
433       cgcccgcgcaccgtgagcggtggccgtctctgcctgcagaacgctcca
(77)       R  P  R  T  V  S  G  G  R  L  C  L  Q  N  A  P
           ʊ  ⌐  β  β  β  β  ⌐  β  β  β  β  β  β  ⌐  ⌐  ʊ  ʊ
481       agggcgactccggcgtacaacgacgctgcggatgccaccgacaaggcc
(93)       R  A  T  P  A  Y  N  D  A  A  D  A  T  D  K  A
           ⌐  ʊ  ʊ  ʊ  ʊ  ʊ  ʊ  α  α  α  α  α  α  α  α  α
529       atcgacggcgtgaaggggggtggccgacgagttgaagaagggcgtggcg
(109)      I  D  G  V  K  G  V  A  D  E  L  K  K  G  V  A
           α  α  α  α  α  α  α  α  α  α  α  α  α  α  α  α
577       gaggctgcggaggccgtctcgggcaacaccgagaaggccgcggaggaa
(125)      E  A  A  E  A  V  S  G  N  T  E  K  A  A  E  E
           α  α  α  α  α  α  α  α  α  α  α  α  α  α  α  α
625       gccggcaagggcgcgagcgaggtggacgcgaaggccaaggacttcggc
(141)      A  G  K  G  A  S  E  V  D  A  K  A  K  D  F  G
           α  α  α  α  α  α  α  α  α  α  α  α  α  α  α  α
673       gagcaggcgaagaaggcgacggaggaggcgtgggacggcgccaaggac
(157)      E  Q  A  K  K  A  T  E  E  A  W  D  G  A  K  D
           α  α  α  α  α  α  α  α  α  α  α  α  α  α  α  α
721       gccgcacagggcatcacggacaaagtcgccgccgcggccaaaaaggaa
(173)      A  A  Q  G  I  T  D  K  V  A  A  A  A  K  K  E
           α  α  α  α  α  α  α  α  α  α  α  α  α  α  α  α
769       gctagctaagctaacactacgttgactagtccgatctgtatcgctcaa
(189)      A  S
           α  α
817       ttcatttttccattgtaaggaatgcatatacgtatttcggtacaagaga
865       taagatagctgtatttattttctgtgatataggattaccgcactgtta
913       atgtcaaacgcaataaagaaaatgattttt
```

FIG. 7

```
AAAAGCCACA AGCCAAGAAC CAATACTTGA TCTGTTGTTT CCTTTAGCTC      50
CCGGAAGACT TTTAGCTGCA CCGATCGATC TCGATC ATG GAG GAT GAG     98
                                        Met Glu Asp Glu

AGG AGC ACC CAG TCG TAC CAG GGA GGT GAG GCC GCC GAG CAG    140
Arg Ser Thr Gln Ser Tyr Gln Gly Gly Glu Ala Ala Glu Gln
  5              10                  15
GTG GAG GTG ACG GAC AGG GGC CTC CTC GGC AAC CTC CTC GGC    182
Val Glu Val Thr Asp Arg Gly Leu Leu Gly Asn Leu Leu Gly
         20              25                  30
AAG AAG AAG GCT GAG GAG GAC AAG GAG AAG GAG GAG GAG CTG    224
Lys Lys Lys Ala Glu Glu Asp Lys Glu Lys Glu Glu Glu Leu
             35              40                  45
GTC ACC GGC ATG GAG AAG GTC TCC GTG GAA GAG CCC GAG GTC    266
Val Thr Gly Met Glu Lys Val Ser Val Glu Glu Pro Glu Val
                 50              55                  60
AAG AAG GAG GAG CAC GAG GAT GGC GAG AAG AAG GAG ACC CTC    308
Lys Lys Glu Glu His Glu Asp Gly Glu Lys Lys Glu Thr Leu
                     65              70
TTC TCC AAG CTG CAC CGA TCC AGC TCC AGC TCC AGC TCG TCT    350
Phe Ser Lys Leu His Arg Ser Ser Ser Ser Ser Ser Ser Ser
 75                  80                  85
AGT GAC GAG GAA GAA GAG GAG GTG ATC GAT GAC AAC GGC GAG    392
Ser Asp Glu Glu Glu Glu Glu Val Ile Asp Asp Asn Gly Glu
         90                  95                 100
GTG ATC AAG AGG AAG AAG AAG AAG GGG CTC AAG GAA AAG CTC    434
Val Ile Lys Arg Lys Lys Lys Lys Gly Leu Lys Glu Lys Leu
            105                 110                 115
CAG GGG AAG CTG CCC GGC CAC AAG GAC ACC GAG GGT GAG CAC    476
Gln Gly Lys Leu Pro Gly His Lys Asp Thr Glu Gly Glu His
                120                 125                 130
GTG ACG GGG CTA CCG GCA CCG GCG GCC CCC GCG TCT GTG CAG    518
Val Thr Gly Leu Pro Ala Pro Ala Ala Pro Ala Ser Val Gln
                    135                 140
ACC CAC GGC GGC CAC CAT GAC ACC GAC GTC GTC GTC GAG AAG    560
Thr His Gly Gly His His Asp Thr Asp Val Val Val Glu Lys
145                 150                 155
ATC GAC GGC GAC GTG AAG ACA GAG GCG GCA CCG GCA GTG CCC    602
Ile Asp Gly Asp Val Lys Thr Glu Ala Ala Pro Ala Val Pro
    160                 165                 170
GAG GAG GAG AAG AAA GGC TTC TTG GAA AAG ATC AAG GAG AAG    644
Glu Glu Glu Lys Lys Gly Phe Leu Glu Lys Ile Lys Glu Lys
                175                 180                 185
CTG CCC GGC GGC CAC AAG AAG CCG GAG GAC GCT GCT GCG GTG    686
Leu Pro Gly Gly His Lys Lys Pro Glu Asp Ala Ala Ala Val
                    190                 195                 200
CCC GTC ACG CAC GCT GCT CCA GCA CCA GTG CAC GCG CCG GTG    728
Pro Val Thr His Ala Ala Pro Ala Pro Val His Ala Pro Val
                        205                 210
CCG GCC CCC GAG GAG GTG AGC AGC CCT GAC GCG AAG GAG AAG    770
Pro Ala Pro Glu Glu Val Ser Ser Pro Asp Ala Lys Glu Lys
215                 220                 225
```

FIG. 8

```
AAG GGC CTG CTG GGC AAG ATC ATG GAC AAG CTG CCT GGT TAC      812
Lys Gly Leu Leu Gly Lys Ile Met Asp Lys Leu Pro Gly Tyr
        230             235             240
CAC AAG ACA GGG GAG GAG GAC AAG GCC GCC GCC GCT ACA GGC      854
His Lys Thr Gly Glu Glu Asp Lys Ala Ala Ala Ala Thr Gly
        245             250             255
GAG CAC AAG CCC AGC GCT TGATCGCCGC CGTGCCCGAG ACCCGTGACC     902
Glu His Lys Pro Ser Ala
        260
GGACCTCGAT TGAATTGTTG GCGTGTGTTG TGTTTGCTTT ACGTCTAAGT       952
TGGTGTCAAG GTGGGAGGGG TTGATCGTCT TTGAAGGTCC GGTCCGTGAA      1002
GCCCGTTCAG TGACGGGTGC TTCTGTTTCA GTTTGGTTCA GAGTCAGGTC      1052
CTGGATGTTG TCAAGTTTGT TTACTTATGG GCACTTGTGT ATTGGTTTAT      1102
TGCTGGGCAT TATGCCTTGA TATTAAAGAT TTCC                       1136
```

FIG. 8 CONTINUED

```
   1   CGAGTGAGGAGCTCAGCGCAAGATGGAGAACCAGGCACACATCGCCGGCGAGAAGAAGGG
  (1)                     M  E  N  Q  A  H  I  A  G  E  K  K  G
  61   CATCATGGAGAAGATCAAGGAGAAGCTCCCCGGCGGCCACGGCGACCACAAGGAGACCGC
 (14)   I  M  E  K  I  K  E  K  L  P  G  G  H  G  D  H  K  E  T  A
 121   TGGTACCCACGGGCACCCCGGCACGGCGACGCATGGTGCCCCGGCCACTGGTGGTGCCTA
 (34)   G  T  H  G  H  P  G  T  A  T  H  G  A  P  A │T  G  G  A  Y│
 181   CGGGCAGCAGGGTCACGCTGGAACCACCGGCACGGGGTTGCATGGCGCCCACGCCGGCGA
 (54)  │G  Q  Q  G  H  A  G  T  T│ G  T  G  L  H  G  A  H  A  G  E
 241   GAAGAAGGGCGTCATGGAGAACATCAAGGACAAGCTCCCTGGTGGCCACCAGGACCACCA
 (74)   K  K  G  V  M  E  N  I  K  D  K  L  P  G  G  H  Q  D  H  Q
 301   GCAGACTGGTGGTACCTATGGGCAGCAGGGACACACCGGCACGGCGACGCATGGCACCCC
 (94)   Q │T  G  G  T  Y  G  Q  Q  G  T  H  G  T  A│ T  H  G  T  P
 361   GGCGACCGGTGGCACCTATGGGCAGCAGGGACATACCGGCACAGCGACGCATGGCACCCC
(114)   A │T  G  G  T  Y  G  Q  Q  G  H  T  G  T  A│ T  H  G  T  P
 421   GGCGACCGGTGGCACCTATGGGGAGCAGGGACACACCGGAGTGACTGGCACGGGGACGCA
(134)   A │T  G  G  T  Y  G  E  Q  G  H  T  G  V  T│ G  T  G  T  H
 481   CGGCACCGGCGAGAAGAAGGGCGTCATGGAGAACATCAAGGAGAAGCTCCCTGGTGGCCA
(154)   G  T  G  E  K  K  G  V  M  E  N  I  K  E  K  L  P  G  G  H
 541   CGGTGACCACCAGCAGACCGGTGGTACCTACGGGCAGCAGGGACACACCGGCACGGCGAC
(174)   G  D  H  Q  Q │T  G  G  T  Y  G  Q  Q  G  H  T  G  T  A│ T
 601   GCATGGCACCCCGGCCGGGGGCGGCACCTATGAGCAGCACGGACACACCGGGATGACCGG
(194)   H  G  T  P  A │G  G  G  T  Y  E  Q  H  G  H  T  G  M  T│ G
 661   CACAGGGACACACGGCACTGGCGAGAAGAAAGGCGTCATGGAGAACATCAAGGACAAGCT
(214)   T  G  T  H  G  T  G  E  K  K  G  V  M  E  N  I  K  D  K  L
 721   CCCTGGTGGCCACGGAGATCACCAGCAGACCGGTGGCACCTACGGGCAGCAGGGACACAC
(234)   P  G  G  H  G  D  H  Q  Q │T  G  G  T  Y  G  Q  Q  G  H  T
 781   CGGCACGGCGACACAGGGCACCCCGGCCGGCGGCGGCACCTATGAGCAGCATGGACACAC
(254)  │G  T  A│ T  Q  G  T  P  A │G  G  G  T  Y  E  Q  H  G  H  T
 841   CGGGATGACCGGCGCGGGGACACACAGCACTGGCGAGAAGAAGGGCGTCATGGAGAACAT
(274)  │G  M  T│ G  A  G  T  H  S  T  G  E  K  K  G  V  M  E  N  I
 901   CAAGGAAAAGCTCCCTGGTGGCCACAGTGACCACCAGCAGACCGGTGGAGCCTACGGGCA
(294)   K  E  K  L  P  G  G  H  S  D  H  Q  Q │T  G  G  A  Y  G  Q
 961   GCAGGGACACACCGGCACGCGACACATGGCACCCCTGCCGGCGGGCACCTACGGGCAGCA
(314)  │Q  G  H  T  G  T  R│ H  M  A │P  L  P  A  G  T  Y  G  Q  H
1021   TGGACACGCTGGAGTGATCGGCACGGAGACGCATGGCACCACGGCCACCGGCGGCACCCA
(334)   G  H  A  G  V  I  G  T  E  T  H  G  T  T  A │T  G  G  T  H
1081   TGGGCAGCACGGACACACCGGAACGACTGGCACTGGGACACACGGCTCCGACGGGATCGG
(354)  │G  Q  H  G  H  T  G  T  T│ G  T  G  T  H  G  S  D  G  I  G
1141   CGAGAAGAAGAGCCTCATGGACAAGATCAAGGATAAGCTGCCTGGACAGCACTGAGCCCG
(374)   E  K  K  S  L  M  D  K  I  K  D  K  L  P  G  Q  H
1201   GTCTGCCCGCGGCCGCTACCCTTGCAGAATAATAACCCCACCGTGTATAAGTTAATTGAG
1261   TCTAGTTCACCTAGCTCACTTGGTCGTTGGAGGAGAGAATGTATTATGTATCTTGGTTTA
1321   AGTTTTCACGGACAACAGTGTGTTCACAGTTTTCTTCTGTTTACACTCTGTAGTGCAAAT
1381   TCGTTTAAGTTTTCACGGACAACAGTGTGTTCACAGTTTTCTTCTGTTTACACTCTGTAG
1441   TGCAAATTTCGTTTTTGTTCTTTTTTTTTTTGTCCATCTTATCCAAGAGACAGACGCAGC
1501   GAAAAAAAAAAAAAAAAAAAAAA
```

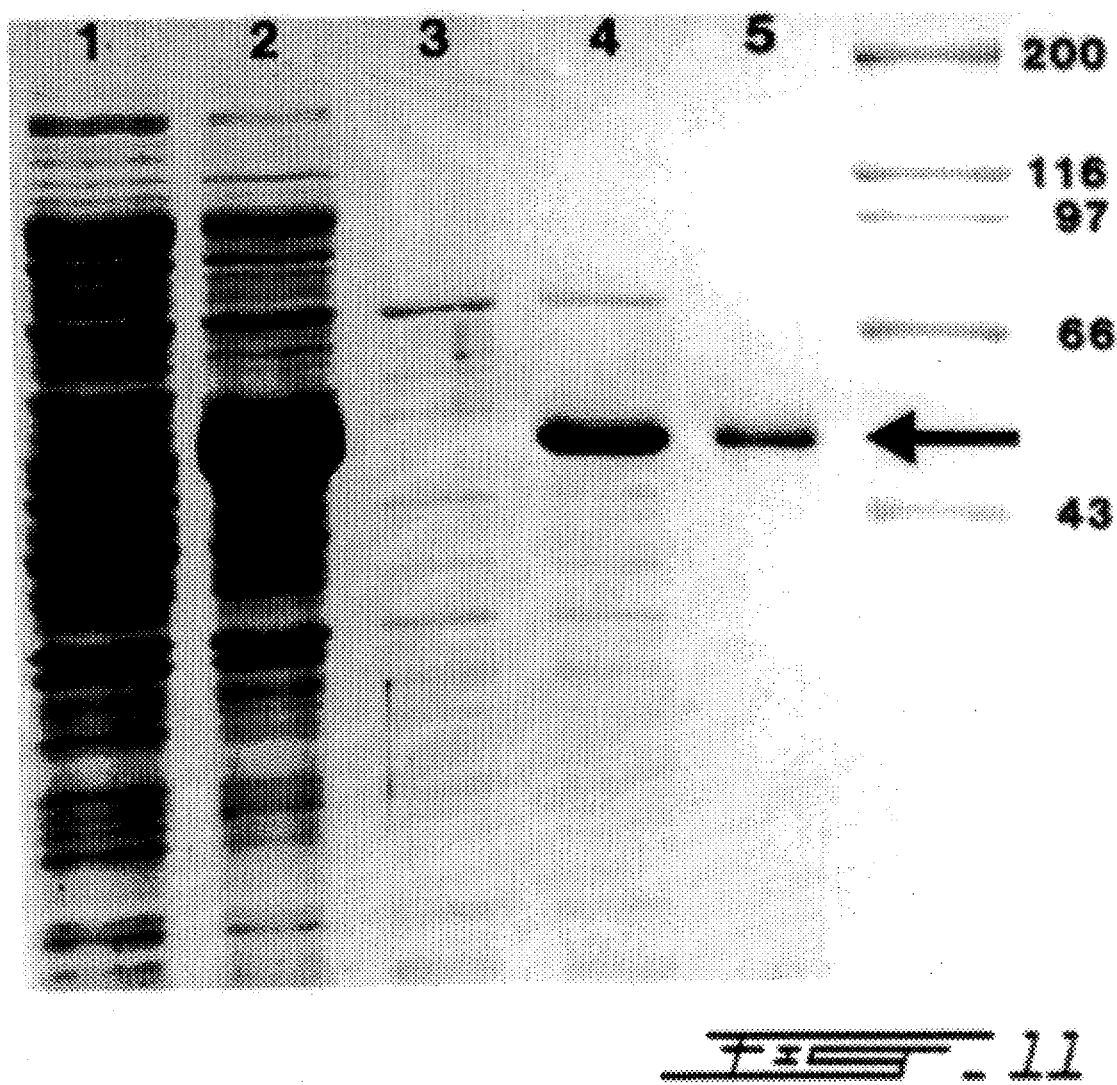

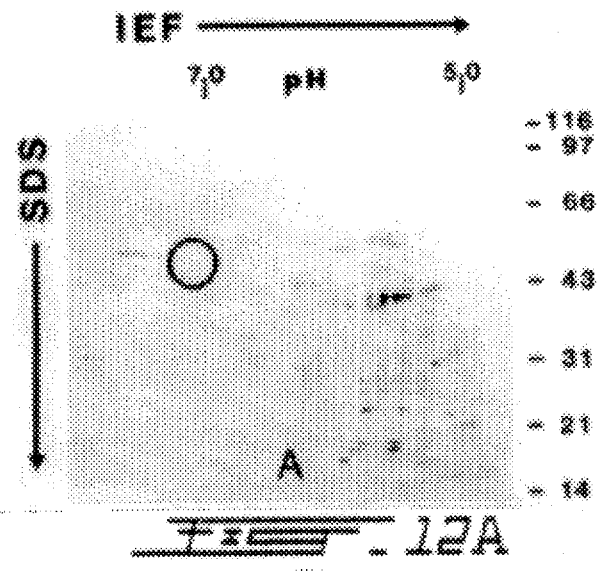

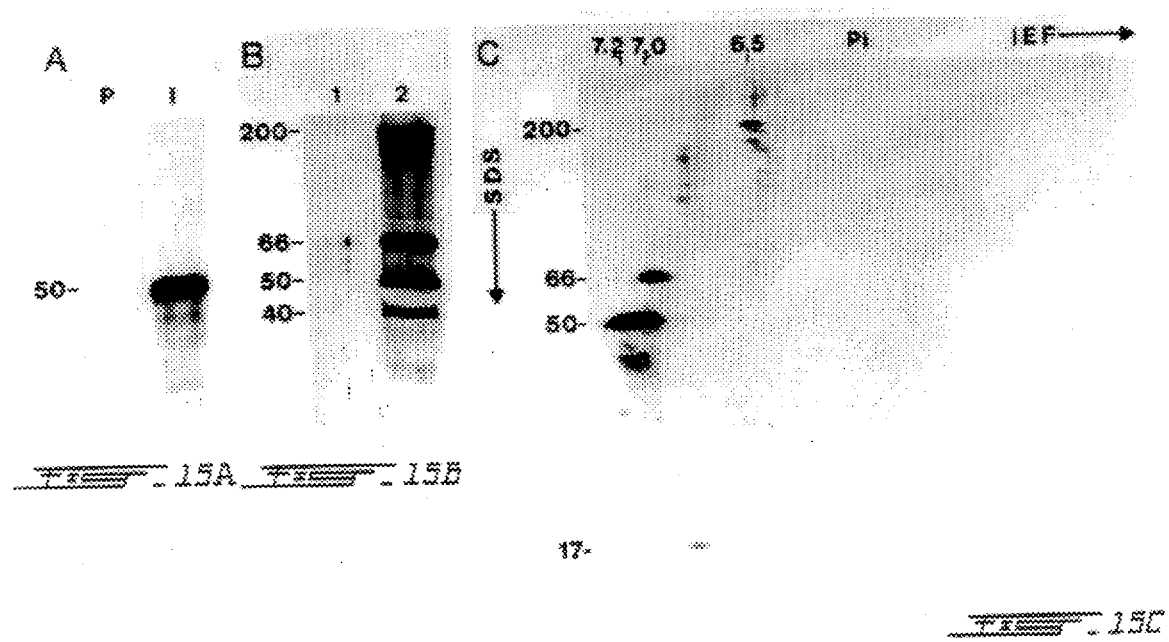

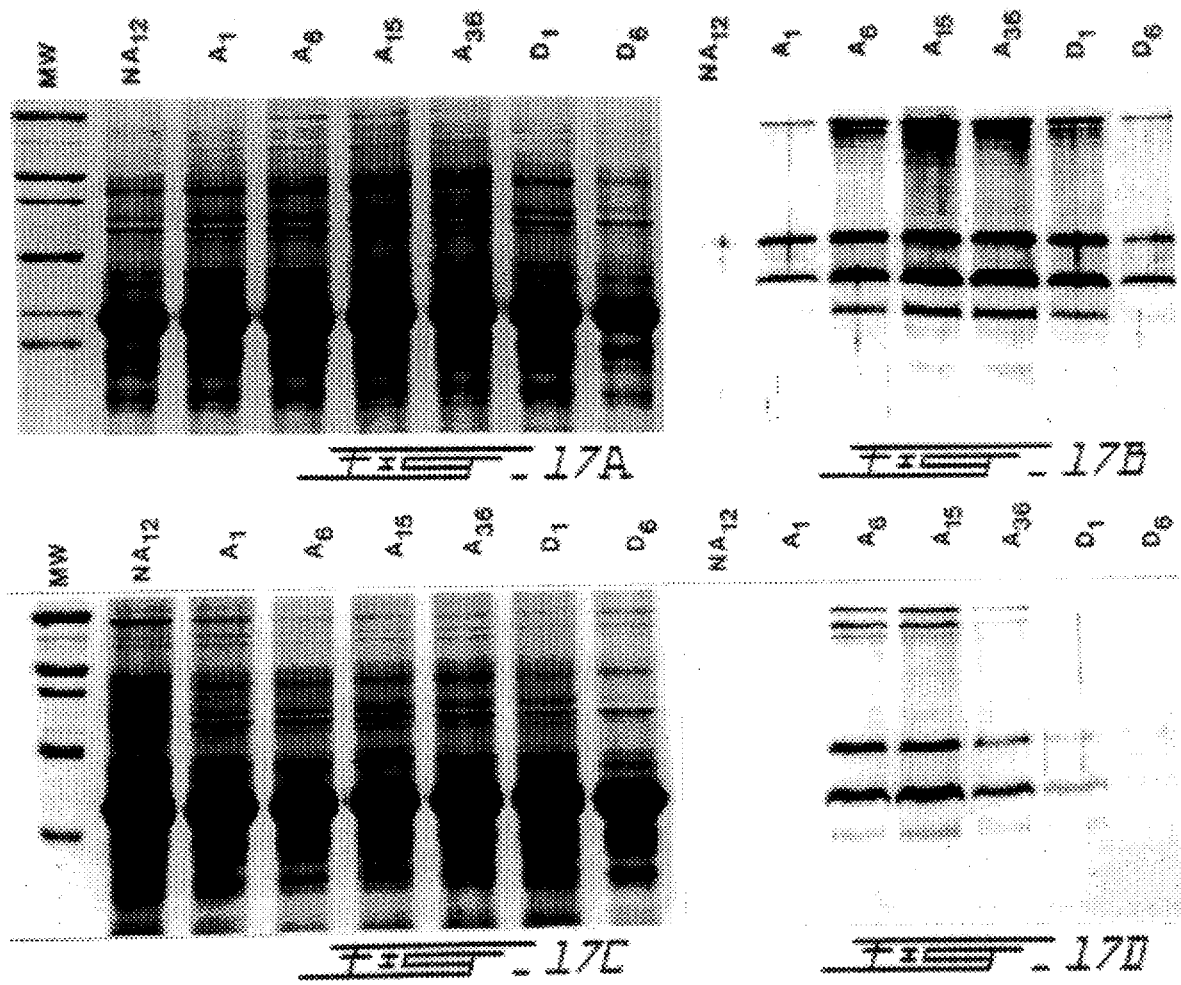

FREEZING TOLERANCE PROTEINS WCS19 AND WCOR410 FROM GRAMINEAE

BACKGROUND OF THE INVENTION

Wheat is a temperate cereal that possesses the capacity to develop a high degree of freezing tolerance (FT) following a period of low temperature growth. In general, winter cultivars, compared to spring ones, possess better protective mechanisms allowing them to optimize growth at low temperature while the induction of FT takes place. This difference is genetically programmed and provides winter cultivars with a competitive advantage to grow at low temperatures. This results in lengthening the growing season since the plant is able to capitalize on favourable conditions that may occur late in the season. Understanding the complexity of this genetic system and its regulation by environmental factors leading to the increase of FT is still a challenge. Development of FT in plants is a metabolically active process induced by low temperature and is associated with altered gene expression [13,42]. Several proteins and their corresponding mRNAs accumulate during cold acclimation. In certain cases, their accumulation was associated with the capacity of plant and tissues to develop FT [15, 31]. Some of these genes are specifically upregulated by low temperature [14, 25, 30, 46] while others are also induced by other factors such as abscisic acid (ABA) and water stress [20, 22, 24]. Sequence analysis of some of these genes has not revealed any information that improves our understanding of their function. Unlike heat shock, water or salinity stresses, FT is not associated with a universal response. The proteins that accumulate during cold acclimation were first believed to be species-specific but recent results indicate that they are family-specific [15, 46]. We have identified a wheat protein family which is upregulated specifically by low temperature and found it to be expressed only in freezing tolerant gramineae species [15]. The kinetics of accumulation and the abundance of these proteins during cold acclimation suggest a close relationship between the development of FT and the amount of these proteins [15]. However, their exact function in FT remains to be established. Since FT is a multigenic trait, the isolation of all the genes involved is required to understand the overall genetical and physiological bases regulating the process of cold acclimation and the induction of FT.

STATEMENT OF THE INVENTION

The present invention relates to a first novel gene regulated specifically by low temperature and associated with the leaf development. This gene, Wcs19, is preferentially expressed in green leaf tissues of tolerant gramineae species and requires both light and low temperature for maximal induction. A second gene has also been sequenced. This gene, Wcs120, encodes a protein which is also induced by low temperature. This gene, also under the scope of the present invention, is very weakly induced by water stress and ABA. Different from the protein encoded by Wcs19, the protein encoded by Wcs120 contains two repeated domains that are highly conserved among RAB (rice abscisic acid-induced) and dehydrin families and appears to be light-independent. The Wcs120 protein does not however contain a serine-rich sequence present in RAB and dehydrin families. Finally, the present invention also relates to a third gene, Wcor410, also induced by low temperature as well as water stress and, to a lesser extend, by ABA. Its expression is light-independent. The protein encoded by this gene contains a serine-rich stretch as found in several drought induced proteins.

DESCRIPTION OF THE INVENTION

Plant Material and Growth Conditions

In this study we used three wheat genotypes: spring wheat (*Triticum aestivum* L. cv Glenlea, $LT_{50}$ −8° C.) and winter wheat (*T. aestivum* L. cv Fredrick, $LT_{50}$ −16° C., cv Norstar, $LT_{50}$ −19° C.), winter rye (*Secale cereale* L. cv Musketeer, $LT_{50}$ −21° C.), barley (*Hordeum vulgare* L. cv Winchester, $LT_{50}$ −7° C.), oat (*Avena sativa* L. cv Laurent, $LT_{50}$ −3° C.), rice (*Oriza sativa*, $LT_5$ 4° C.), alfalfa (*Medicago falcata* cv Anik, $LT_{50}$ −12° C., canola (*Brassica napus* cv Jet neuf, $LT_{50}$ −16° C.). FT was determined as reported previously [31] and expressed as the temperature required to kill 50% of the seedlings ($LT_{50}$).

Seeds were germinated in moist sterilized vermiculite for 5 days in the dark and 2 days under artificial light at 25° C./20° C. (day/night) with a 15 h light period at an irradiance of 250 $\mu mol.m^{-2}.s^{-1}$. Control plants were maintained under the same conditions while cold acclimation was performed by subjecting the seedlings to acclimation conditions (6° C./2° C. day/night, 10 h photoperiod). In the case of rice exposed to low temperature, the day/night cycle was of 10°/5° C. For ABA treatment, 7-day old seedlings were watered daily for 4 days with nutrient solution containing $10^{-5}M$ ABA. As expected, ABA-treatment plants showed a reduced growth rate compared with the control, indicating that ABA elicited the proper physiological response. Water stress was induced by withholding water until the plants became visibly wilted (4 days). Heat shock was performed by incubating seedlings at 40° C. for 3 h. This treatment was sufficient to induce typical heat shock proteins as described in our previous work [7]. Salt-stressed plants were grown for 18 h in solutions containing 500 mM NaCl. Anaerobic treatment was accomplished by submerging seedlings under water in an airtight container for 24 h. Wounding was performed by slicing leaves to 1 cm pieces and floating on water for 14 h. Etiolated seedlings were grown in complete darkness. Deacclimation was performed by returning cold-acclimated plants (36 day at 4° C.) to normal growth conditions for 1 and 5 days.

Preparation of Calli

The calli used in this study were derived from winter wheat (*T. aestivum* L. cv Fredrick). Plants were grown under the same environmental conditions mentioned above, using a mixture of soil:peat:vermiculite (1:1:1;v/v/v) supplemented with a soluble fertilizer (N:P:K 20:20:20). Inflorescences were tagged at the onset of anthesis and the spikes were harvested 12 days postanthesis. The kernels were surface-sterilized as described earlier [4]. The embryos were aseptically isolated and cultured on Murashige and Skoog [27] (MS) medium supplemented with 30 $g.l^{-1}$ sucrose, 10 $\mu M$ 2,4-dichlorophenoxyacetic acid (2,4-D) and 0.8% Difco Bacto Agar (pH 5.7). The cultured plates were incubated at 24°/20° C. with a 15 h photoperiod under low irradiance (100 $\mu mol.m^{-2}.s^{-1}$). The callus cultures were maintained by subculturing every 2 weeks on the same medium. Low temperature exposure of calli was done at 6°/2° C. (day/night).

Construction and Screening of the cDNA Library

Poly(A)$^+$ RNA was isolated from cold-acclimated winter wheat Norstar [8]. A cDNA library was constructed in lambda ZAPII (Stratagene) using EcoRI-Not I linkers from Pharmacia, and transformed into *Escherichia coli* strain XL-1 blue using techniques well known in the art. The subtractor kit from Invitrogen was used in accordance with manufacturer's directives to generate a cDNA subtracted probe, prepared from poly(A)⁺ RNA isolated from cold-acclimated and non-acclimated winter wheat plants. The plaques showing an increased hybridization signal with the subtracted probe or by differential screening (14) (clones pWcs19, pWcor410 and pWcs120) were selected and purified, and subcloned via the automatic excision process described by Stratagene. The screening of the library and all the recombinant DNA techniques were performed using techniques well known in the art [36].

Northern and Southern Blot Analyses

Poly(A)⁺ RNA (4 μg) or total RNA (10 μg) samples were mixed with ethidium bromide before electrophoresis on formaldehyde agarose gels [35]. This allowed visual evaluation of RNA quality and loads on gels. A clone previously isolated, p2.1, that did not display differential hybridization during cold acclimation was also used to verify the equal loading of RNA. After electrophoresis, RNA or DNA was transferred to nitrocellulose membranes (BAS-85, Schleicher & Schuell) in 20× SSC. The filters were air-dried and then baked for 1 h at 80° C. prior to hybridization with the ³²P-labelled pWcs19, pWcor410 or pWcs120 inserts [33]. Filters were washed at 65° C. with several buffer changes of decreasing SSC concentration (5 to 0.1×) and then autoradiographed on Kodak XRP films with intensifying screens (DuPont, Cronex Lightning plus) at −80° C.

Genomic DNA was prepared from shoots of 8-day old seedlings as previously described [34], and DNA samples (10 μg) were digested with appropriate restriction endonucleases prior to electrophoresis.

DNA Sequence Analysis

Plasmid DNA was prepared, and deletion subclones were generated using exonucleases III and VII, as described [48]. Plasmids were sequenced by the dideoxynucleotide chain-termination method [37] with the aid of T7 and Gene-ATAQ kits from Pharmacia. Sequence comparison was carried out with the Genetic Computer Group's Sequence Analysis Sofware package, version 6.0, with a Vax computer (Université de Montréal). The database was searched with the TFASTA program. The hydropathy profile was calculated according to Kyte and Doolittle [18], using a 6 aa window. Secondary structure predictions were made by the method of Garnier et al. [11].

In Vitro Transcription/Translation pWcs19: pWcs19 was linearized by digestion with Hind III and the coding strand was transcribed in vitro with T3 RNA polymerase. The reaction volume of 20 μl contained 5 mM MgCl2, 50 mM Tris-HCl pH 7.5, 10 mM DTT, 2 mM spermidine, 10 U of RNase inhibitor, 0.5 mM ATP, 0.5 mM GTP, 0.5 mM CTP, 0.5 mM UTP, 500 ng of linearized plasmid and 40 U of T3 RNA polymerase (Pharmacia). Nucleic acids were extracted with phenol:chloroform:isoamyl alcohol (25:24:1) and precipitated with ethanol. The pellet was resuspended in TE buffer (10 mM Tris-HCl, pH 8.0, 1 mM EDTA) and translated in vitro using a wheat germ extract from Promega in presence of ³⁵S-methionine, according to manufacturer's directives. Translation products were fractionated on SDS-PAGE, dried and exposed to Kodak XOMAT-AR film.

pWcs120: Plasmid pWcs120 was mutated using polymerase chain reaction to introduce a NdeI restriction site at the ATG start codon and a BamHI site just after the stop codon. For this purpose, two oligonucleotides were synthesized using the Gene Assembler from Pharmacia. The first oligonucleotide, 5'-AGTGAGGATCCCAGCGCCATATGGAG AAC-3' (SEQ ID NO:2), was homologous to the coding strand of Wcs120 with the exception of four nucleotides to introduce BamHI and NdeI sites. The second oligonucleotide, 5'-GTTGTCCGGTGGATCCTTAAAC-3' (SEQ ID NO:8), was complementary to the coding strand with the exception of three nucleotides to produce a BamHI site. Amplification using the TagI DNA polymerase (Perking-Elmer Cetus corporation) and subcloning into pUC9 (IBI) and pET (Novagen) vectors was performed. The inserted, amplified fragment was then digested with NdeI and BamHI and ligated into NdeI-BamHI-digested plasmid pET11a. This placed the entire coding frame, including the start methionine codon, directly downstream of the T₇ promoter to allow a high level of expression in *E. coli*. Expression was performed in BL21 (DE3) (Novagen). At a bacterial density measured by the value of absorbance at 600 nm ($A_{600}$) of 0.6, 1 mM IPTG was added to the bacterial suspension, and 3 h later the bacteria were collected by centrifugation and resuspended in 0.1 volume of electrophoresis buffer for analysis.

To purify the expressed protein, bacterial cells were suspended in 5 to 10% of the culture volume of 50 mM Tris (pH 8.0), 10 mM EDTA. After one freeze-thaw cycle, the cells were disrupted by sonication and the lysate was centrifuged at 15,000 g for 20 m in to eliminate insoluble proteins. The boiling-stable proteins were precipitated from the supernatant with ice-cold acetone and collected by centrifugation. The proteins were solubilized in electrophoresis buffer and separated on a 10% preparative polyacrylamide gel. The expressed protein was excised and electroeluted for 3 h. The eluted protein was then precipitated with acetone and analyzed by two-dimensional gel electrophoresis as previously described.

To compare the *E. coli*-expressed protein with that synthesized in vitro, Poly(A)⁺ RNA from cold-acclimated and non-acclimated wheat were translated in a wheat germ system and analyzed by two-dimensional gel electrophoresis as previously described.

The cDNA clones Wcs19, Wcor410 and Wcs120 were identified from cold-acclimated wheat shoots of the cultivar Norstar. Based on reprobing the library with the purified inserts, the representation was estimated to be 0.02% and 0.1% for Wcs19 and for Wcs120, respectively. The isolated clones hybridize preferentially to mRNAs of 1.0, 1.3 and 1.65 kb, for Wcs19, Wcor410 and Wcs120, respectively, that accumulate upon exposure to low temperature.

BRIEF DESCRIPTION OF DRAWINGS

FIG. 1. Kinetic analysis of Wcs19 mRNA expression during cold acclimation. Poly(A)⁺ RNA (4 μg per lane) was separated and transferred to nitrocellulose membranes as described in M & M and hybridized with ³²P-labelled cDNA insert from pWcs19. $NA_7$ and $NA_{12}$, control plants (non-acclimated) grown for 7 and 12 days at 20° C. $A_1$, $A_6$ and $A_{36}$, plants cold-acclimated for 1, 6 and 36 days; $D_1$ and $D_5$, cold-acclimated plants (36 days) were deacclimated for 1 and 5 days at 24° C. Formaldehyde gels were visualized with ethidium bromide and the clone p2.1 was used to control the equal loading and quality of RNA (not shown). A. Winter wheat Fredrick, B. Winter wheat Norstar, C. Spring wheat Glenlea.

FIG. 7. DNA sequence and deduced amino acid sequence of Wcs19 (SEQ ID NO:1 and SEQ ID NO:2, respectively). The coding strand has been determined using T3 and T7 RNA transcription of Wcs19 in the Bluescript vector (Stratagene) and subsequent hybridization to RNA from acclimated plants. The longest ORF is shown here (570 nucleotides). The consensus polyadenylation signal is shown as a double underline; proline residues are boxed; acidic residues (D and E) are circled. On a third line, secondary structure predictions were made by the method of Garnier et al. [11]. Symbols are: α, alpha helix; β, beta sheet; ⊥, turns; σ, random coil. GenBank Accession No.: L13437.

FIG. 8. Nucleotide and deduced amino acid sequence of Wcor410 (SEQ ID NO:5 and SEQ ID NO:6, respectively). The initiating and terminating codons are underlined.

FIG. 9. Nucleotide and deduced amino acid sequence of the Wcs120 (SEQ ID NO:3 and SEQ ID NO:4 respectively). The DNA sequence was obtained on both strands by the chain termination method. Domain A (repeated 6 times) is underlined, and domain B (repeated 11 times) is boxed. GenBank Accession No.: M93342.

FIG. 11. SDS-PAGE analysis of proteins present in E. coli transformed with plasmid pEWcs120. Lane 1, nontransformed; lane 2, transformed and induced with 1 mM IPTG; lane 3, nontransformed boiled extract; lane 4, transformed and induced boiled extract; lane 5, induced purified protein. The proteins were analyzed on a 10% polyacrylamide gel and visualized by staining with Coomassie blue R-250. The arrow indicates the present of the 50-kD protein in pWEcs120-transformed cells induced with IPTG. The molecular mass markers are shown on the right side (kD).

FIG. 12. Two-dimensional gel electrophoretic analysis. A, In vitro translation produces of mRNAs isolated from control (nonacclimated) winter wheat Fredrick. B, In vitro translation produces of mRNAs isolated from cold-acclimated winter wheat Fredrick. Circle indicates the 50 kD-protein induced during cold acclimation. C, Purified protein expressed in E. coli transformed with pWEcs120. The protein had identical molecular weight and isoelectric point as that synthesized in vitro and in vivo.

FIG. 15. Immunoblot characterization of anti-Wcs120 antibody. A. Purified Wcs120 protein used for immunization. P, preimmune serum, I, affinity purified immune serum. B. Lane 1, soluble proteins from nonacclimated wheat (cv. Fredrick) seedlings; lane 2, 36 day cold-acclimated wheat seedlings. C. Proteins were isolated from winter wheat cv. Fredrick cold-acclimated for 36 days, and separated on a 2 D gel. After transfer to nitrocellulose, the filter was incubated with the anti-Wcs120 antibody and processed. Several proteins in the basic portion of the gel.

FIG. 17. Accumulation kinetics of freezing tolerance markers (FTMs) in *Triticum Aestivum* L. cv. Fredrick and cv. Glenlea. A. Coomassie Blue-stained gel of cv. Fredrick. B. Parallel gel transferred to nitrocellulose and probed with the purified anti-Wcs120 antibody. C. Coomassie blue-stained gel of cv. Glenlea; 50% more proteins were loaded compared with A. D. Parallel gel transferred to nitrocellulose and probed with the purified anti-Wcs120 antibody. $NA_{12}$ non-acclimated 12 day old plants; $A_1$, $A_6$ and $A_{15}$ and $A_{36}$, cold-acclimated for 1, 6, 15 and 36 days; $D_1$ and $D_6$, deacclimated for 1 and 6 days. The plants used in the deacclimation experiment had been cold-acclimated for 36 days. High molecular weight markers (Bio-Rad) are shown on the left side.

RESULTS the kinetic studies using northern blot analysis (FIGS. 1 and 2) show that the accumulation of Wcs19 and Wcs120 is very rapid, and remains at a constant level throughout the acclimation period in both freezing tolerant cultivars, Fredrick and Norstar. On the other hand, in the less tolerant cultivar Glenlea, the expression of these mRNAs declines despite maintaining the plants at 4° C. When the plants were deacclimated at 24° C. the steady-state level of Wcs19 and Wcs120 transcripts declined rapidly. FIGS. 3 and 4 show that the Wcs19 and Wcs120 mRNAs were not induced by water stress, exogenous ABA application or heat shock. Positive controls were used to demonstrate that the treatments elicited the typical molecular responses in addition to the physiological ones described above. Other treatments such as wounding, anaerobic and salt stresses did not shown any effect on the expression of Wcs genes (not shown). These results indicate that the accumulation of Wcs19 and of Wcs120 is specifically induced by low temperature. The expression of Wcor410 (results not shown) is regulated by low temperature in freezing tolerant monocots only and correlates with the capacity of plants and varieties to develop freezing tolerance. This gene was also induced to a similar level by water stress and to a lesser extend by ABA.

Figures 2A, 2B, 2C:
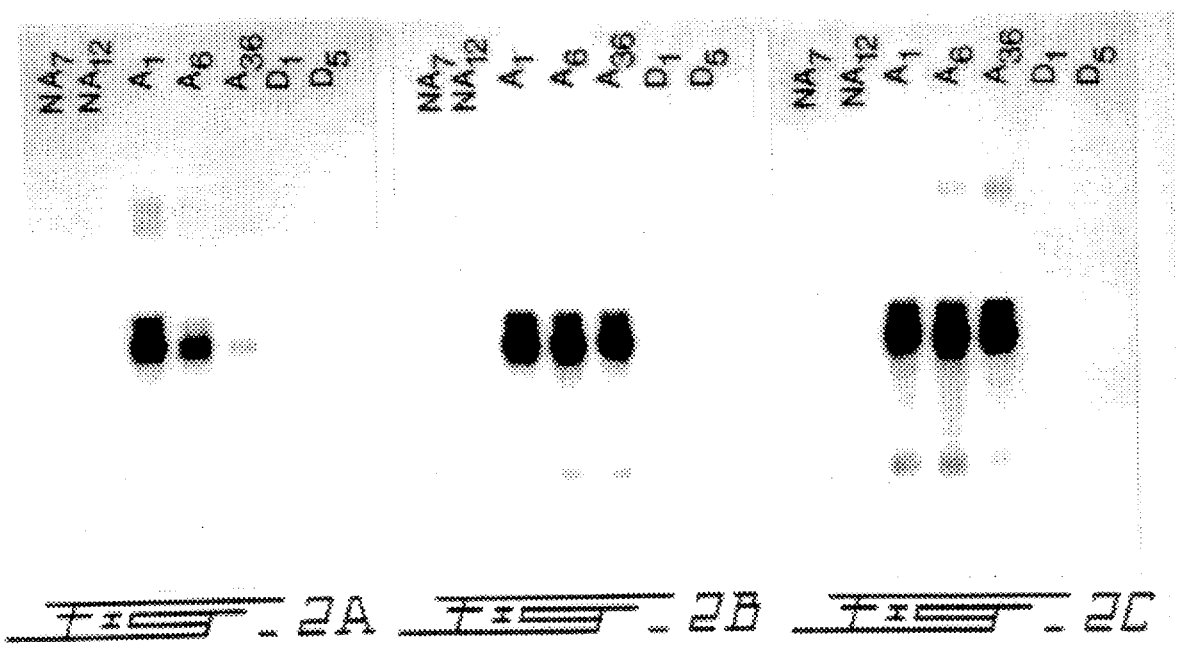
FIG. 2. Northern blot analysis of mRNA hybridized with Wcs120 during cold acclimation and deacclimation of wheat. Poly(A)+ RNAs (4 µg) isolated from nonacclimated, cold-acclimated, and deacclimated wheat plants were separated by agarose gel electrophoresis in the presence of formaldehyde and then transferred to nitrocellulose membranes. The blots were probed with $^{32}$P-labelled cDNA insert from plasmid pWcs120. The final wash was at 55° C. in 0.1× SSC containing 0.1% SDS. Bands were visualized by autoradiography. A control probe (p2.1) was used to verify the equal RNA loading on the gel. $NA_7$ and $NA_{12}$, control plants (nonacclimated) grown for 7 and 12 d; $A_1$, $A_6$, and $A_{36}$, plants cold acclimated for 1, 6 and 36 d; $D_1$ and $D_5$, plants deacclimated for 1 and 5 d. The plants used in the deacclimation experiment had been cold acclimated for 36 d. A, Glenlea; B, Fredrick,; C, Norstar. Exposure was for 2 h.
Figure 3A:
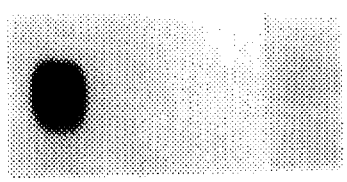
FIG. 3. Northern blot analysis of total RNA (10 µg per lane) from wheat plants (cv Fredrick) exposed to different treatments. A. The filter was hybridized with Wcs19. 1, plants cold-acclimated for one day; 2, plants water-stressed for 4 days; 3, plants treated with $10^{-5}$M ABA for 4 days; 4, non-acclimated plants grown at 24° C. 5, plants heatshocked for 3 h at 40° C. B. The filter was hybridized with Wab1, an ABA-responsive clone isolated from wheat in our laboratory. Lanes 1 to 4 as in A. C. The filter was hybridized with HSP70B cDNA (StressGen, Victoria, B.C., Canada). 1, plants grown at 24° C.; 2, plants heat-shocked for 3 h at 40° C.
Figure 3B:
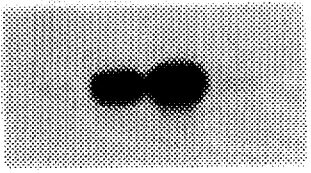
Figure 3C:
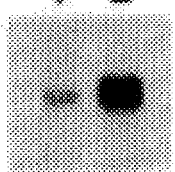
Figure 4:
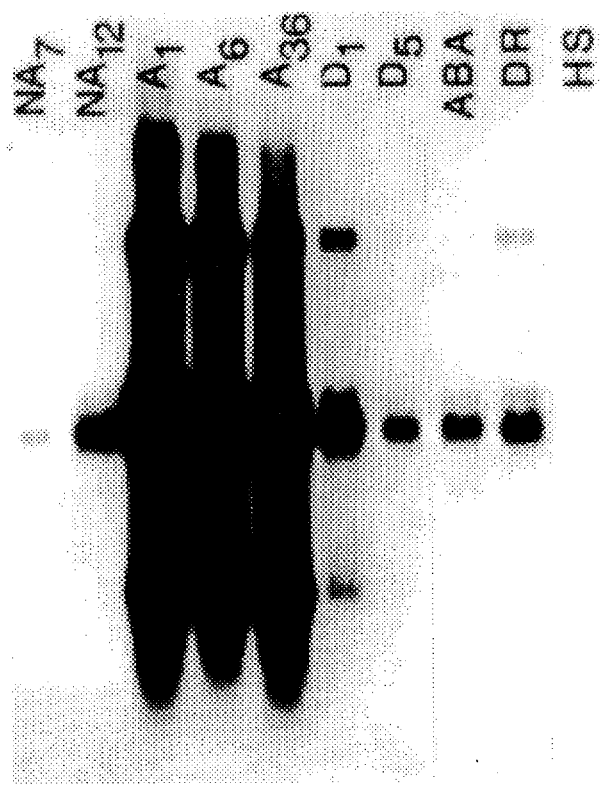
FIG. 4. Northern blot analysis of mRNA hybridized with Wcs120 after different treatments. Poly(A)+ RNAs (4 µg) isolated from plants grown as described were separated and probed as described in FIG. 2. ABA, plants treated with ABA for 4 d; DR, water-stressed plants visibly wilted; HS, plants treated at 40° C. for 3 h. Other symbols as in FIG. 2. Exposure was for 20 h.
Figure 5A:
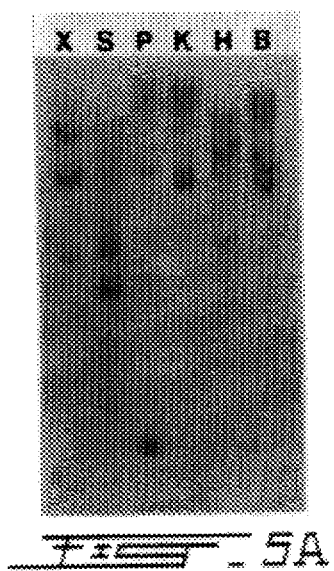
FIG. 5. Southern blot analysis of wheat genomic DNA. Wheat DNA from three genotypes was digested with 6 different restriction enzymes, separated by agarose gel electrophoresis, transferred to nitrocellulose and then probed with Wcs19. X, Xba 1; S, Sac 1; P, Pst 1; K, Kpn 1; H, Hind III; B, Bam H1. A, Glenlea; B, Norstar; C, Fredrick.
Figure 5B:
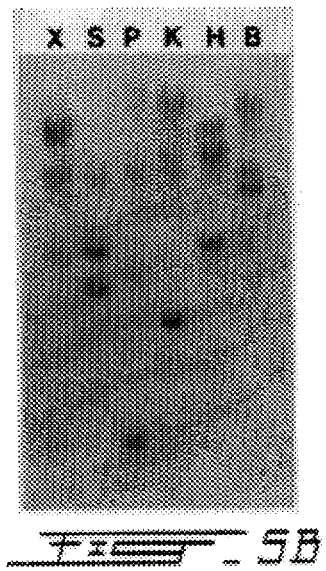
Figure 5C:
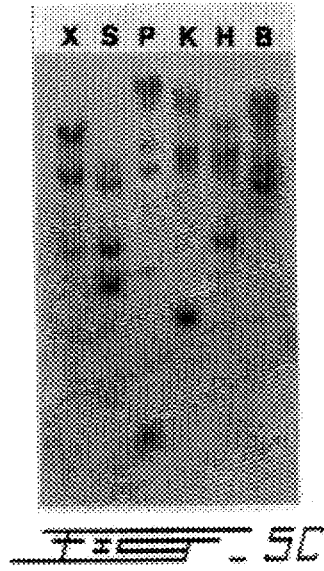
Figure 6A:
FIG. 6. Southern blot analysis of wheat genomic DNA. Wheat DNA (10 µg) form three genotypes was digested with 12 different restriction enzymes, separated on agarose gel electrophoresis, transferred to nitrocellulose, and then probed with Wcs120. Lane 1, ApaI; lane 2, KpnI; lane 3, SacI; lane 4, HindIII; lane 5, PstI; lane 6 PvuII; lane 7, BamHI; lane 8, EcoRI; lane 9, XbaI; lane 10, SalI; lane 11, XhoI; lane 12, SmaI. A, Glenlea; B, Fredrick; C, Norstar.
Figure 6B:
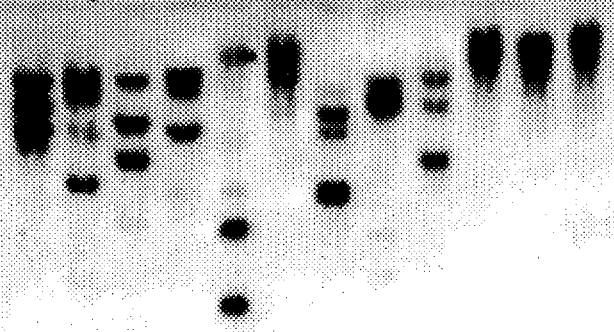
Figure 6C:
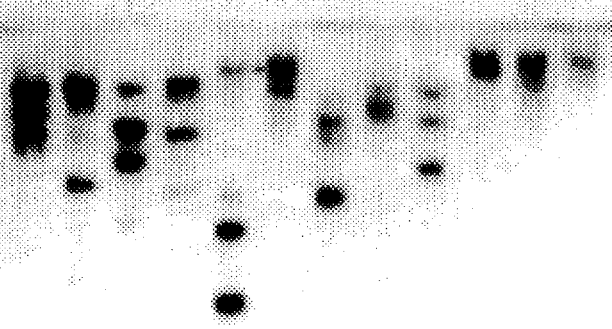

Southern analysis, shown in FIGS. 5 and 6, using probes Wcs19 and Wcs120, did not reveal any differences in the restriction pattern between the three genotypes. This result suggests that the reduced expression of Wcs19 and of Wcs120 in the less tolerant cultivar is not due to the detectable difference in the genomic organization of the gene or in the relative gene copy number since the bands intensities are comparable.

Sequence Analysis

The complete DNA and amino acid sequences of Wcs19, Wcor410 and Wcs120 are shown in FIGS. 7, 8 and 9. Because of the degeneracy of codons, it is understood that any DNA sequences encoding the same amino acid sequences are under the scope of the invention. It is also understood that conserved amino acid substitutions in similar sequences as determined by techniques well known in the art are under the scope of this invention. Such conservative substitutions are frequently encountered, when comparing sequences of molecules which have diverged from a common ancestor. In different varieties of a same species, for instance in *T. aestivum* L. cv Winoka (a variety of wheat), conservative substitutions are encountered in a proteic sequence closely related to pWcs120 protein [50]. Long open reading (ORF) frames were found in both DNA orientations. Northern blots were thus probed with labelled RNAs produced by in vitro transcription of the inserts using the T3 or T7 promoters and corresponding RNA polymerases. The predicted polypeptides encoded by Wcs19, Wcor410 and Wcs120 are 190, 262 and 390 amino acids in length and have a calculated molecular mass of 19, 28 and 39 kDa and a pI of 8.8, 5.1 and 7.7, respectively.

Wcs19: Search of the Genbank database revealed no homology with any protein. However, at the DNA level, a significant homology was found with a cold regulated partial DNA sequence (pT59) from barley [3]. The sequence analysis indicates that the protein is alanine-rich (21%) and has high content of glycine (8%), lysine (8%) and proline (7%). These four amino acids represent 44% of the polypeptide. The protein has a particular charge distribution. The acidic amino acids aspartate and glutamate (FIG. 7, circled) are localized towards the C-terminal half and thus give this region a net negative charge of −7. Furthermore, this region (from aa 100 to the end) has a high propensity to form an alpha helix as observed for some transcription factors [32]. The N-terminal half is rich in proline (boxed), lysine and arginine, and has a net positive charge of +10. The hydropathy profile (not shown) indicates that most of the protein is hydrophilic except between amino acids 42 and 59.

Wcor410: This protein is rich in glutamate (16%) and has a compositional bias for charged amino acids (43%). It also contains a succession of 9 serine residues as found in several drought induced proteins (see FIG. 8).

Wcs120: The predicted protein has a compositional bias for Gly (26.7%), Thr (16.7%), and His (10.8%). These three amino acids account for 54% of the polypeptide, whereas Cys, Phe, and Trp are absent. The predicted protein contains two repeated domains. The A repeat is basic and has the consensus sequence GIKKGVMENIKEKLPGGHGDHQQ (SEQ ID NO:9), which is repeated six times in the ORF (underlined in FIG. 9). The B repeat contains 14 amino acids (consensus sequence TGGTYTQQGHTGTT (SEQ ID NO:10)) and is repeated 11 times.

A computer search revealed that repeats A and B are found in the dehydrin and RAB protein families, with the exception that the B repeat was not found in dehydrins 8 and 9. Outside these repeats, very little homology was found between Wcs120 and these two protein families with the exception that all the predicted polypeptides start with ME and, at the carboxy tail, share a stretch of 18 highly conserved amino acids ending with QH. These similarities suggest that Wcs120 could share a function with the dehydrins and RAB families. On the other hand, the conserved sequence SGSSSSSSS (SEQ ID NO:11), found in all RAB and dehydrin proteins, was conspicuously absent in Wcs120.

Figure 10:
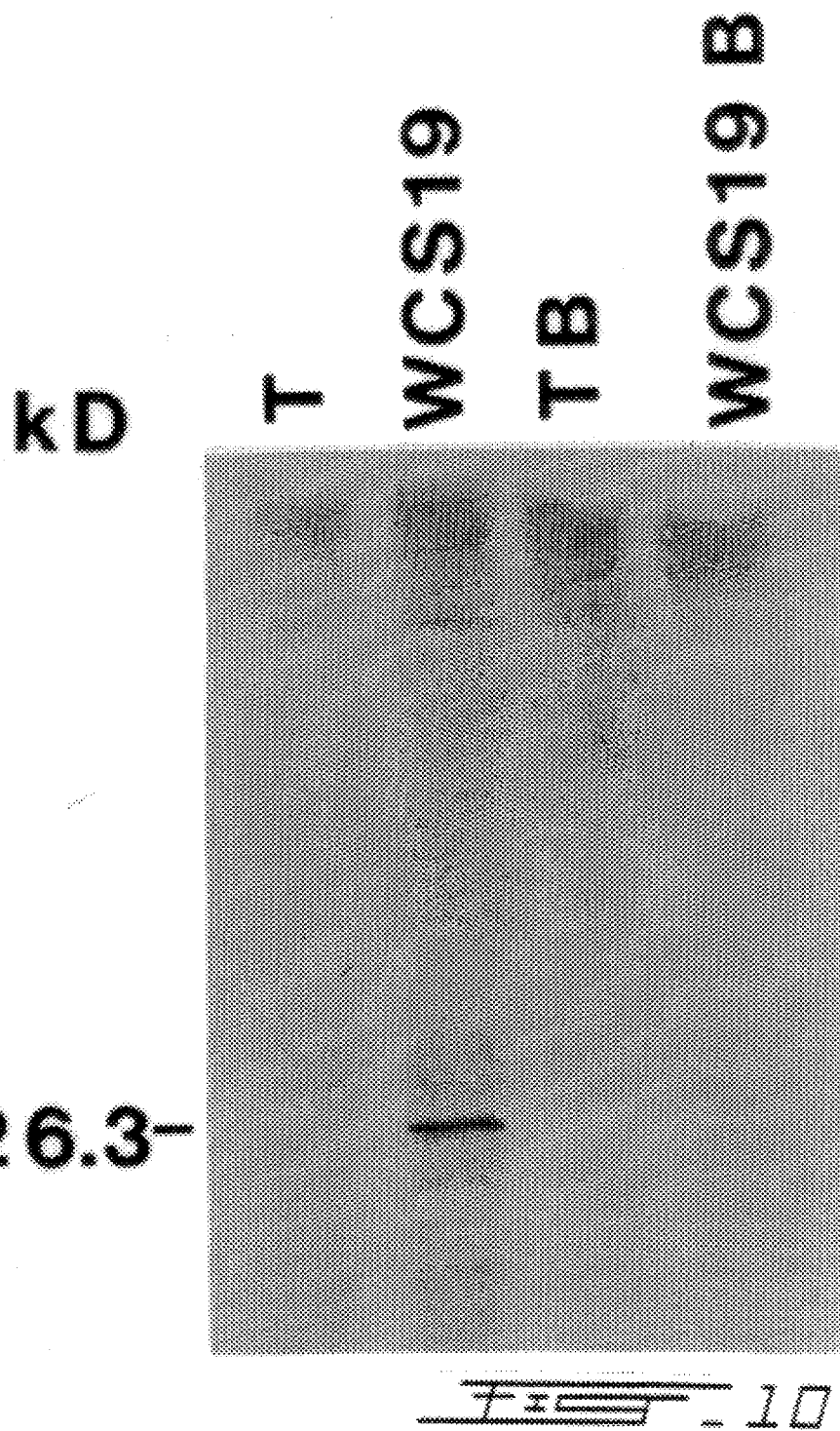
FIG. 10. In vitro transcription/translation of pWcs19. The labelled translation produces were separated on SDS-PAGE and visualized by autoradiography. T, translation produces of the linearized vector along; Wcs19, translation products of the linearized pWcs19, TB and Wcs19B, the translation produces were boiled for 10 min.

In vitro transcription/translation experiments with Wcs19 were performed as described above. FIG. 10 shows a specific translation produce of 26 kDa (lane Wcs19). The apparent MW of 26 kDa is higher than the predicted mass of 19 kDa. This discrepancy has already been observed for several other stress proteins [14, 15]. Since three other ATG start codons present in the 5' region of the cDNA are followed by in frame stop codons, we determined whether the longest ORF identified was able to encode the same protein. This ORF was subcloned using the polymerase chain reaction and the transcription/translation experiment was repeated with the subclone. The same translation product size was obtained indicating that the ATG at position 205 is the first one that can be used and that the stop codons identified before this ATG cannot be due to sequencing errors. The proper stop codon is found at position 775, and the consensus polyadenylation signal is found at position 924. The product of translation does not remain in solution after boiling as shown in lane Wcs19B and is thus different from other alanine- and glycine-rich stress proteins cloned up to date [5, 14, 16, 20, 30].

To identify the Wcs120 encoded protein, the Wcs120 ORF was expressed in *E. coli*. The protein was purified from *E. coli* (FIG. 11) and compared with the in vitro translation produces of RNA isolated from nonacclimated and cold-acclimated plant (FIG. 12). The protein synthesized by bacteria was boiling stable and co-migrated with a 50-kD protein produced by mRNAs isolated from the cold-acclimated plants. The protein produced in the bacteria also co-migrated with a protein that accumulated in vivo during cold acclimation, suggesting that little or not posttranslational modifications were occurring in the intact plants and that, in both species, the first initiation codon, at position 23, was probably used. A discrepancy between the calculated and apparent molecular masses on SDS-PAGE was observed (39 versus 50 kD). This discrepancy likely results from the avid binding of SDS, as suggested for other plant stress proteins with skewed amino acid composition.

Tissue and Species Specificity

Figure 13A:
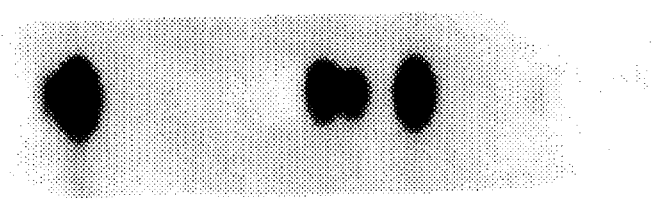
FIG. 13. Tissue and species specificity of Wcs19 expression. Total RNA (10 µg per lane) was isolated from the different tissues. Plants and calli were cold-acclimated for 6 days. Panel A. lanes A, B and C, root, crown and leaf tissues of cold-acclimated wheat tcv Fredrick); lane D, non-acclimated wheat leaves; lanes E and F, cold-acclimated and nonacclimated wheat calli. G to M, cold-acclimated species. Lanes: G, Brassica; H, alfalfa; I, rice; J, rye; K, barley; L, oat; M, wheat. Lanes N to T correspond to the non-acclimated tissues of G to M respectively. Panel B. Ethidium bromide-stained gel.
Figure 13B:
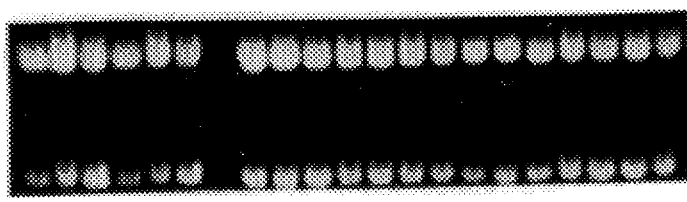

Northern blot analysis of Wcs19 mRNA expression in root, crown and leaf tissues of acclimated wheat seedlings are shown in FIG. 13. The results indicate that the Wcs19 expression is specific to leaf tissue. The expression was hardly detected in root and crown. To determine if the expression is strictly associated with the leaf structure, the expression of the gene in non-differentiated tissues such as wheat calli was compared to that of leaves. The results in FIG. 13, lane E, show that no accumulation of mRNA occurs during calli acclimation to low temperature. Furthermore, there was not detectable expression in other tissues such as the flower parts, developing or mature embryos (not shown). These results demonstrate that the Wcs19 mRNA accumulation is leaf-specific and is not directly needed for the acquisition of FT in other tissues. The accumulation of Wcs19 mRNA was found to be present in most cereal species that can cold acclimate and suggests that it may play a crucial role in the leaf acclimation to low temperature. The highest levels of accumulation was found in the most tolerant species, wheat and rye, compared to that of barley, a less tolerant species. Oat and rice did not show any accumulation of Wcs19. On the other hand, the two dicot tolerant plants examined, Brassica and alfalfa did not show any induction. This indicates that the Wcs19 is gramineae-specific and that its expression is correlated to the capacity of each genotype to develop FT.

On the other hand, when using an antibody anti-Wcs120, it appears that freezing tolerance markers are retrieved in leaves as well as in crown and roots. The more tolerant parts (leaves and meristematic crown) contain more of these markers than less tolerant parts of plants (roots and basal region of the crown). This could means that tissue-specificity of Wcs120 is different from Wcs19 or that the antibodies raised against Wcs120-encoded protein can recognize the protein Wcs120 and other related proteins which distribution is different from Wcs19.

Light Requirement

Figure 14A:
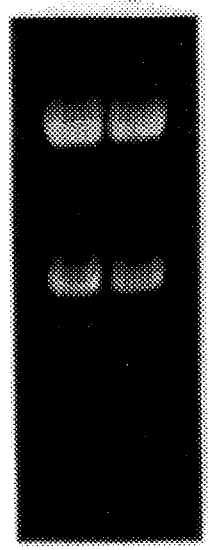
FIG. 14. Light requirement for the expression of Wcs19. Total RNA (10 µg per lane) was isolated from etiolated wheat seedlings (cv Fredrick) cold-acclimated in the dark (lane 1) or in the presence of light (lane 1) for 4 days. A, ethidium bromide-stained gel; B, the filter was hybridized with Wcor410, a cold-regulated clone isolated in our laboratory; C, the filter was hybridized with Wcs19.
Figure 14B:
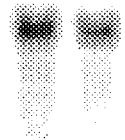
Figure 14C:

The association of Wcs19 expression to the leaf tissue and its complete absence in the non-photosynthetic tissues drew our attention to the possibility that light may be required for expression. The results in FIG. 14 show that light is required for maximal mRNA accumulation since etiolated plants accumulated at least 4 fold less Wcs19 transcripts. The cold-regulated gene Wcor410 was not affected by the presence or absence of light (FIG. 14B). This result confirms the light stimulation of Wcs19. In addition, as for cold-acclimated callus cultures, albino seedlings lacking chloroplastic structures and chlorophyll (generated from some callus cultures) were not able to accumulate any detectable amount of Wcs19 transcript in the presence of light and low temperature (not shown). These results indicate that the Wcs19 expression is dependent on organized leaf tissue and that light acts as a stimulating factor.

When using antibodies anti-Wcs120, the expression of the freezing tolerance markers was not limited to photosynthetic tissues and was not light-dependent.

Development of Antibodies to Select for Freezing Tolerance

Antibody production and purification

Antibodies against Wcs120 were generated using antigen synthesized in *E. coli* [14]. The purified protein was used to generate antibodies in a New Zealand rabbit. Preimmune serum was taken from the rabbit before the first immunization and immune serum was taken 10 days after the second and subsequent injections.

For antibody purification, the purified Wcs120 protein was coupled to Affi-gel 10 (Bio Rad) at 3 mg/ml of bed resin in 0.1M HEPES buffer, pH 7.5 containing 80 mM $CaCl_2$. The coupling was performed at 4° C. overnight. Free sites were saturated with 0.2M ethanol-amine for 1 h. The coupled resin was washed with phosphate buffered saline (PBS) containing 0.1% NP-40 and the serum was incubated for 1 h with the beads. After washing with PBS, the bound antibodies were eluted with 0.3M glycine, pH 2.0 and immediately neutralized with TRIS base. The purified antibodies were then dialyzed against PBS and lyophilized.

Protein Extraction, Separation and Immunoblot Analysis

Soluble proteins were extracted from different tissues by grinding in a precooled mortar with TRIS buffer [0.1M TRIS-HCl, pH 9.5 containing 1 mM phenylmethylsulfonyl fluoride (PMSF)]. The extract was immediately centrifuged for 5 min at 12000 g and the supernatant was adjusted to final buffer concentration with 5× SDS electrophoresis sample buffer [19]. Samples were separated by electrophoresis on 10% polyacrylamide-SDS gels (SDS-PAGE) or on two-dimensional (2 D) gels as described [8].

Total soluble proteins separated by SDS-PAGE were electrophoretically transferred to nitrocellulose (BAS-85, Schleicher and Schuell). After blocking with powdered milk (2%) in PBS containing 0.2% Tween-20 (Blotto), the blot was incubated with a 1:1000 dilution of the purified Wcs120 antibody. After washing with PBS-Tween, the proteins recognized by the primary antibody were revealed with alkaline phophatase coupled to anti-rabbit IgG as secondary antibody. The complex was revealed by incubating in 100 mM Tris, pH 9.5, 100 mM NaCl, 5 mM $MgCl_2$, 0.2 mg/ml nitroblue tetrazolium, and 0.2 mg/ml of 5-bromo-4-chloro-3-indolyl phosphate.

Northern Blot Analysis

RNA isolation and Northern blot analysis were as previously described [14] except that washing stringency was lowered to 5× SSC at 55° C.

Specificity of Anti-Wcs120 Antibody

The purified Wcs120 protein produced in the bacterial system and proteins extracted from control and cold acclimated wheat seedlings were separated by SDS-PAGE and transferred to nitrocellulose. Preimmune serum did not react with the Wcs120 protein while the purified anti-Wcs120 antibody recognized the 50 kDa protein expressed in *E. coli* and that synthesized in cold acclimated seedling (FIG. 15). No proteins were recognized in the control non-acclimated plant. The anti-Wcs120 antibody also recognized several other proteins from cold acclimated seedlings. Analysis by 2 D gel electrophoresis (FIG. 15C) revealed that they were neutral to slightly basic (from pI 6.5 to 7.3) and correspond to proteins previously identified during cold acclimation by in vivo labelling of proteins and by in vitro translation of mRNA isolated from cold acclimated plants [8].

Northern Blot Analysis of Wcs120 Related mRNAs

Figure 16:
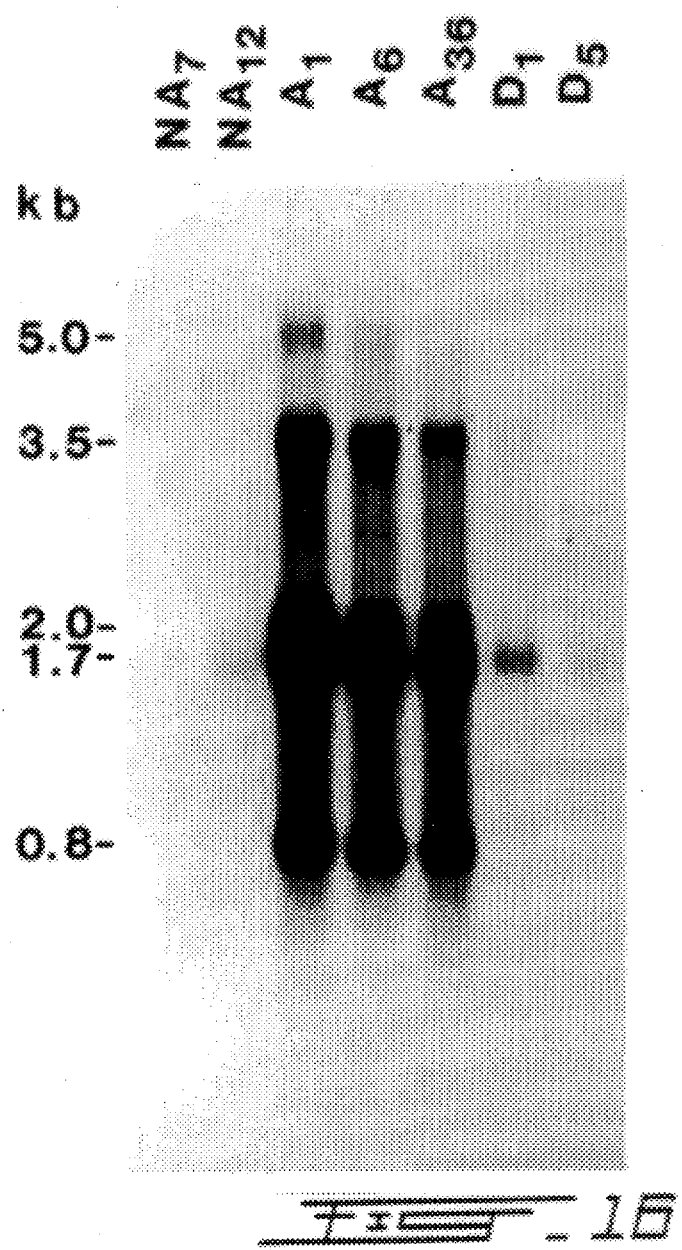
FIG. 16. Northern Blot analysis of winter wheat cv Fredrick mRNA after cold acclimation and deacclimation. Poly (A)+ RNAs (4 µg) isolated form non-acclimated, cold-acclimated, and deacclimated wheat plants were separated by agarose gel electrophoresis in the presence of formaldehyde and then transferred to a nitrocellulose membrane. The blots were probed with $^{32}$P-labelled cDNA insert from clone pWcs120 and bands were visualized by autoradiography. One major band of 1.7 kb and four minor bands varying in size from 0.8 to 5 kb were detected. $NA_7$ and $NA_{12}$ non-acclimated 7 and 12 days plants; $A_1$, $A_6$ and $A_{36}$, cold-acclimated for 1, 6 and 36 days; $D_1$ and $D_5$, deacclimated for 1 to 5 days. The plants used in the deacclimation experiment had been cold-acclimated for 36 days.

The anti-Wcs120 antibody identified at least four protein groups on 1 D and 2 D gels. In order to examine whether this homology was apparent at the mRNA level, we probed a Northern blot with the pWcs120 insert and washed it at low stringency (55° C. 5× SSC). Five mRNA species, ranging in size from 0.8 to 5 kb, were detected (FIG. 16). This low stringency washing condition allowed us to detect three new mRNA species that were not seen at higher stringency [14]. these mRNAs may encode the different proteins recognized by the anti-Wcs120 antibody. We have recently isolated several anti-Wcs120 positive clones. One of these has a cDNA insert size of 4.7 kb and encodes the 200 kDa protein [30]. We thus believe that the proteins revealed by the anti-Wcs120 antibody are encoded by different genes.

Accumulation Kinetics of Freezing Tolerance Markers (FTMs) During Cold-acclimation The anti-Wcs120 antibody was reacted against soluble proteins isolated from cold-acclimated seedlings. Equal amounts of proteins separated by gel electrophoresis were used in assays in any given cultivar. Since the cultivar Glenlea is relatively freezing sensitive, it is likely to synthesize less FTMs and, therefore, 50% more proteins were loaded to increase the chance of immunodetection (compare FIG. 17A and 17C). Results in FIG. 17B show that proteins from non-acclimated seedlings react very weakly to this antibody. When the seedlings were transferred to 4° C. FTMs accumulated rapidly. A large amount of these proteins was seen after 6 days of cold acclimation in both Fredrick (more tolerant) and Glenlea (less tolerant) cultivars. The accumulation of these FTMs was more pronounced and began earlier in Fredrick (FIG. 17B) and the level was maintained or continued to increase slightly during the 36 days of cold treatment. On the other hand, these FTMs had reached their maximum levels in Glenlea after 15 days of cold acclimation and they then declined despite the seedlings being maintained at 4° C. When the plants were returned to normal growth conditions, the FMTs declined rapidly and reached near control level after 6 days of deacclimation for Fredrick and after only 1 day for Glenlea. These results indicate that the accumulation of FTMs is correlated with the capacity of each genotype to develop freezing tolerance during the cold acclimation period.

Figure 18A:
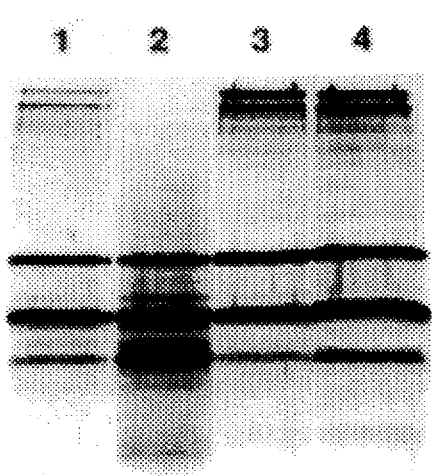
FIG. 18. Immunoblot analysis of FTMs isolated from different tissues and from plants grown in different conditions. A. Proteins isolated from different plant tissues (cold acclimated cv. Fredrick) and probed with the purified anti-Wcs120 antibody. Lane 1, root; lane 2, basal region of the crown; lane 3, meristematic crown; lane 4. leaf. B. Effect of different growth conditions of FTMs isolate from shoot tissue. Lane 1, *Triticum aestivum* L. cv, Fredrick cold-acclimated for 36 days; lane 2, salt-treated cv. Fredrick; lane 3, water-stressed cv. Fredrick; lane 4, absoisic acid-treated cv. Fredrick; lane 5, heat-shocked cv. Fredrick; lane 6, *Hordeium vulgare* L. cv. Winchester cold-acclimated for 36 days; lane 7, water-stressed cv. Winchester.

Expression of FTMs in Different Tissues and During Other Stresses and ABA Treatments On comparing the relative abundances of these proteins in leaves, crown and roots, we concluded that FTMs accumulate to higher levels in those parts of the plant with the highest freezing tolerance. FIG. 18A shows that the leaves and meristematic crown (more tolerant) contain more FTMs than the basal region of the crown and roots (less tolerant).

Figure 18B:
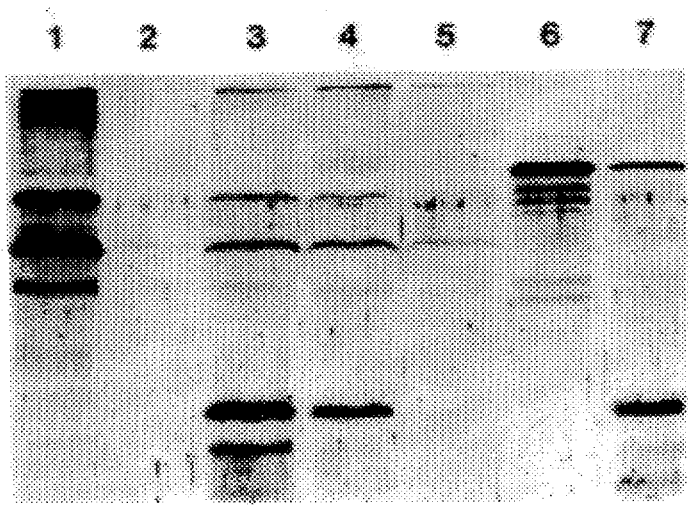

FTMs are specifically induced by low temperature (FIG. 18B). These proteins are slightly induced by water stress and ABA, while they are not induced by heat shock or salt stress. Interestingly, the antibodies recognized proteins of lower molecular weight (14 to 21 kDa) that are strongly induced by water stress and ABA. These proteins presumably belong to the RAB and/or dehydrin families since proteins of that molecular weight range have been shown to be induce during water stress and ABA treatments [43, 47, 5]. Furthermore, the Wcs120 sequence shares homology with these two protein families through two repeated motifs [14]. In order to verify that dehydrins are recognized by our antibody, barley seedlings were subjected to water stress and the soluble proteins were extracted and reacted with the anti-Wcs120 antibody. The results in FIG. 18B show that the low molecular weight proteins strongly induced during water stress were not detected in cold-treated barley. Moreover, a protein of ca. 72 kDa was strongly induced by cold treatment while it was only slightly induced by water stress. This indicates that proteins strongly induced by cold treatment are induced either poorly or not at all by water stress.

The role of ABA in the induction of freezing tolerance was investigated in two wheat (*T. aestivum* L.) cultivars, Glenlea (spring var) and Fredrick (winter var). Exogenous application of ABA ($5\times10^{-5}M$ for 5 days at 24° C.) increased the freezing tolerance of intact plants by only 3° C. ($LT_{50}$) in both cultivars. Maximal freezing tolerance ($LT_{50}$ of −9° C. for Glenlea and −17° C. for Fredrick) could only be obtained with a low temperature treatment (6/2; day/night) for 40 days. These results show that exogenously applied ABA cannot substitute for low temperature requirement to induce freezing tolerance in intact wheat plants. Furthermore, there was not increase in the endogenous ABA level of wheat plants at any time during low temperature acclamation, suggesting the absence of an essential role for ABA in the development of freezing tolerance of intact plants. On the other hand, ABA application ($5\times10^{-5}M$ for 5 days at 24° C.) to embryogenic wheat calli resulted in an increase of freezing tolerance similar to that achieved by low temperature. However, as in intact plants, there was no increase in the endogenous ABA level during low temperature acclimation of calli. These results indicate that the induction of freezing tolerance by low temperature is not associated with an increase in ABA content. Using the anti-Wsc120 antibody specific to a protein family associated with the development of freezing tolerance, we demonstrated that the induction of freezing tolerance by ABA in embryogenic wheat calli was correlated with the accumulation of a new 32 KDa protein. This protein is specifically induced by ABA but shares a common antigenicity with those induced by low temperature. These results suggest that ABA induces freezing tolerance in wheat calli via a regulatory mechanism different from that of low temperature.

Species Specificity of FTMs

Figure 19:
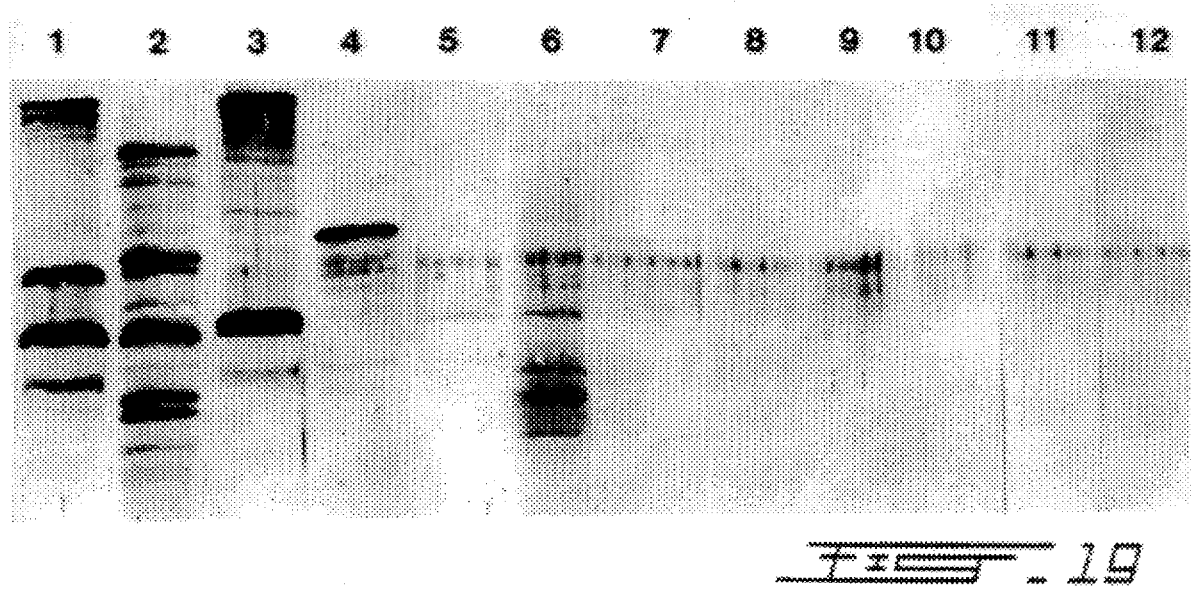
FIG. 19. Immunoblot analysis of soluble proteins isolated from different cold-acclimated species. Lane 1, *Triticum aestivum* L. cv. Fredrick; lane 2, *Agropyron repens* L.; lane 3, *Secale cereale* L. cv. Musketeer; lane 4, *Hordeum vulgare* L. cv. Winchester; lane 5, *Avena sativa* L. cv. Laurent; lane 6, *Phleum pratense* L.; lane 7, *Zea mays*; lane 8, *Oryza sativa*; lane 9, *Brassica naput* L.; lane 10, *Mentha canadensis*; lane 11, *Petunia hydrida*; lane 12, *Medicago falcata* cv. Anik.

In order to determine whether proteins similar to Wcs120 accumulate during cold acclimation in other species, we examined a number of tolerant and less tolerant cereals as well as four tolerant dicot species. FIG. 19 shows that proteins from tolerant cereals (lanes 1–3) reacted most strongly with the anti-Wcs120 antibody. Less tolerant cereals (lanes 4–6) reacted less strongly. It appears that the correlation between $LT_{50}$ and FTMs may not be perfect for all graminaceous species, as shown in the case of oat (lane 5). The antibody did not recognize any protein in the sensitive cereal varieties (lanes 7 and 8) or within the tolerant dicotyledonous group (lanes 9–12). This suggests that these FTMs are not associated with cold acclimation in these species or that the proteins have evolved in a way that does not allow cross-reactivity with the antibody.

The Wcs120 cDNA was shown to hybridize with at least five different mRNA species, which have the potential to encode all the proteins recognized by the anti-Wcs120 antibody. The accumulation kinetics of these coordinately expressed proteins are positively correlated with the time of development of the degree of freezing tolerance. Hence, we refer to this protein family as Freezing Tolerance Markers [FTMs]. The winter wheat variety Fredrick accumulates more of these FTMs and continues accumulating them throughout the cold acclimation period. In contrast, the spring variety Glenlea accumulates less FTMs and their level starts to decline early during the acclimation period correlating with the sharp reduction in mRNA seen in our previous study [14]. Moreover, FTMs accumulated in greater amounts in tissues with higher capacity to develop freezing tolerance. This observation is consistent with our earlier observation, which showed a preferential synthesis of the 200 kDa protein (a member of this protein family) at the shoot level compared with the roots [31].

We have also demonstrated that the antibody recognizes several proteins in other cold-acclimated cereals. The amount of cross-reactive material was much higher in the freezing-tolerant species. These results confirm the positive correlation between the induction of these proteins and the capacity of plant or tissues to develop freezing tolerance. Furthermore, the accumulation of this protein family did not appear to be associated with the plant developmental stage since it was induced at low temperature in calli, sprouts, and germinating seedlings at different growth stages (not shown). The expression of FTMs was induced to the same level in dark or light-grown seedlings, suggesting that this is light independent.

No cross-reactivity could be found in freezing-tolerant dicotyledonous species suggesting that freezing tolerance in monocots and dicots involves different proteins. However, these proteins may have similar properties (such as boiling stability or high hydrophilicity). The present of proteins of variable molecular weight having a similar antigenicity is novel and suggests that their function is determined through common small repeated elements within their structure. Such repeats do exist within the 50 kDa [14] and 200 kDa proteins [30]. Similar motifs have been found in the dehydrins [5, 1] and RAB [43, 47] families. These results suggest that the number of repeats within the protein molecule and the amount of these proteins synthesized are important factors in the acquisition of freezing and drought tolerance. However, the induction of proteins of different sizes during cold and drought stress (in both wheat and barley) suggests that they probably have distinct functions with some complementarity.

Some of the FTMs induced by cold are also induced slightly by water stress and ABA but they are not induced by salt stress or heat shock. Evidence in the literature indicates that ABA and drought can increase freezing tolerance [6, 10, 39]. However, in the case of the intact wheat plant, the freezing tolerance conferred by ABA is –8° C. (–4° C. for the non-acclimated control) compared with –16° C. after cold acclimation [10, 31]. This may be due to the partial induction of FMTs and other cold-regulated genes necessary for the acquisition of freezing tolerance. This assumption requires a detailed study to determine the exact role that ABA and drought may play during cold-acclimation. It is however interesting to observe that small molecular weight proteins recognized by the anit-Wcs120 antibodies are present in high concentration during water stress and ABA treatment. This suggests that low temperature induction of freezing tolerance involves pathways distinct from that induced by ABA and water stress. A similar conclusion has been reached in studies, with *Arabidopsis thaliana* [28].

The characterization of FTMs should help us understand their role in the acquisition of freezing tolerance. However, the antibody represents a very important and easily accessible tool to identify cereal cultivars with a superior capacity for cold acclamation. This potential can be assessed rapidly with proteins extracted from as little as 50 mg of plant tissues. This provides breeders with a simple and economic method of selection for potential freezing tolerance of new cereal crops.

Understanding the molecular genetic bases of cold acclimation in wheat requires the identification of genes involved in this complex mechanism. Towards this goal, we have identified and characterized several cDNA clones [14, 15, 30]. The cDNA clones Wcs19, Wcor410 and Wcs120 described here represent novel genes which are regulated by low temperature. These clones were identified by screening a cDNA library with a subtracted probe to reduce the high signal of abundant mRNAs and thus facilitate the isolation of new cDNAs. Northern analyses have shown that the mRNAs accumulate only when the plants are exposed to low temperature. After 24 hours of exposure, the three genotypes accumulated mRNAs to nearly their maximal levels indicating that the accumulation is very rapid. The mRNA levels remained constant thereafter in the two winter genotypes while it declined in the less tolerant spring genotype after 36 days of low temperature exposure. This result suggests that a constant level of mRNAs may be necessary to allow the accumulation of a sufficient amount of proteins required for the development of FT. Southern analysis has not shown any differences in restriction patterns between the most tolerant and less tolerant genotypes. One might infer that the promoter structure is different and could not be detected by simple restriction analysis. This possibility is not likely since all genotypes accumulate the cold-induced mRNAs to similar levels at early stages of cold acclimation. We do not yet understand the mechanism underlying this differential expression.

Our results indicate these mRNAs are expressed specifically in tolerant gramineae species. There was no detectable expression in sensitive gramineae such as rice or in any of the tolerant dicot species examined. However, this does not exclude the possibility that proteins with a similar function are present in dicots. Moreover, genes Wcs19 and Wcs120 are not induced by ABA, drought, heat shock, salt, wounding, or anaerobic stresses indicating that the gene is induced specifically by low temperature. Sequence comparison of Wcs19 did not reveal any homology with other published genes or with other genes cloned in our laboratory. Furthermore, we have not found any of the repeated sequences observed in RAB [26], dehydrins [5], or LEA [1] while such repeated sequences were found in Wcs120. This suggests that Wcs19 plays a distinct role in cold acclimation. Several structural properties of this protein are similar to those found in transcription factors. The C-terminal half of the protein contains all the acidic residues with a net charge of −7. In addition, alpha helical structure is predicted for the last 91 amino acids. It has been suggested that an alpha helical structure might be an essential element of the activating region of several transcription factors [32]. Furthermore, the acidic character of the activating region is an important feature which allows transcription factors to interact with RNA polymerases and increase transcription rates [32]. It has been shown that the overall RNA polymerase activity increases markedly during cold acclimation [38]. This could contribute to increase the expression of several genes important for the development of FT.

Another important feature of transcription factors is the presence of a positively charged domain. This domain is essential for the interaction with DNA. In Wcs19, the N-terminal half is rich in proline (14%) and contains basic residues (lysine and arginine) with a net charge of +10. Those characteristics are found in transcription factors such as CPRF-1 [44], HBP1-a [41], and CTF/NF-1 [23]. However, detailed experiments are required to confirm this hypothesis.

Our results indicate that Wcs19 expression is leaf-specific and not directly associated with FT in other plant tissues or callus cultures. It seems that its expression is dependent on leaf tissue organization and on the plant capacity to acclimate at low temperature. The role of leaf during cold acclimation is to provide the energy required for the development of FT. Photosynthesis is responsible for the production of this energy and it has been shown that tolerant cultivars have a higher photosynthetic capacity than the spring one [2, 29]. This modulation of the photosynthetic apparatus by the tolerant plants to optimize growth at suboptimal conditions is correlated with an increased resistance to photoinhibition [29]. The close correlation of Wcs19 gene expression with the capacity of leaves to develop FT suggests that this gene may play a role in the process.

The specific expression in the leaf indicates that cell or callus cultures mimic only in part the response of intact plants to low temperature stress. Our results emphasize that the leaf tissue response could be very important to the survival of the whole plant. It appears from these observations, and that of other [3, 21, 46], that we must distinguish between cellular responses to low temperature which may be ubiquitous to all cells from the tissue-specific reactions. This is an important consideration when one wants to improve FT at the whole plant level.

On the other hand, the present of repeated sequences in Wcs120 in common with RAB and dehydrins indicate a common feature or function. A high proportion of hydrophilic residues is present in all three protein families, as is the case of LEA proteins present in maturing embryos [1], and for cold-induced proteins found in other plants [3, 9, 17], in insects [49], and in E. coli [12]. The absence of hydrophobic regions indicated that these proteins are probably not membrane-bound.

It has been reported for wheat and Arabidopsis that several polypeptides induced are accumulated during cold treatment remain soluble during boiling in aqueous solution [7, 20]. This property was previously observed for LEA proteins and dehydrins [5, 16]. The large number of hydrophilic residues probably confers a very flexible backbone and this is likely responsible for boiling stability of these proteins, including the 50 kD protein identified in our work (Wcs120), because they would not have to renature after boiling. The high Gly content (26%) of the 50-kD protein may confer a high flexibility and mobility to the protein as found in several Gly-rich proteins such as elastin. The small size of the Gly molecule and its short side chain gives it a unique function in the structure of several proteins. It facilitates the formation of intramolecular hydrogen bonding and thus gives the protein a random coil conformation. This property allows the protein to stretch, bend, and expand in all directions, a property that could be useful to protect cellular structures against freezing or severe dehydration. Physicochemical characterization of this protein should help to verify this assumption. The significance of these properties is still unclear but the high hydrophilicity may also be important in hydrogen bonding to the lattice of nascent ice crystals, thus modifying the structure or propagation of ice crystals, which may reduce intracellular freezing damage during winter. The high hydrophilicity of these proteins may also be important in trapping enough water inside the cell to prevent local dehydration that may occur during freezing or water stress [13, 40].

Drought stress was shown to increase the freezing tolerance [13]. This suggests that some features must be common between the proteins induced during these different stresses.

The absence of the serine-rich repeat and the specific induction of Wcs120 mRNA early during cold acclimation, before any increase in osmotic pressure, cell dehydration, or ABA content occurs (data not shown), suggested that the Wcs120 gene was regulated differently from the RAB and dehydrin families. The molecular mass of the Wcs120 protein is much higher than the known RAB and dehydrin protein masses. The striking recurrence of the common repeats in Wcs120, RAB, and dehydrin proteins suggests that survival at low temperature and during water stress requires large amounts of these unusual proteins.

Protective effect of purified proteins on the denaturation of glutathione reductase by different treatments.

The inventors have evaluated the protective effect of the purified proteins Wcs120 and Wcor410 on the denaturation of glutathione reductase by different treatments.

Denaturation of glutathione reductase (Type III, Sigma) was performed by incubating 14 mU of enzyme in 50 µl of 100 mM $KPO_4$ buffer pH 7.5. The starting activity was measured and this value was set at 100% of activity (control). The different preparations were incubated either alone (GR alone) or in the presence of the indicated amount of purified proteins. Bovine serum albumin was purchased from Pharmacia (BSA, DNase free 10 mg/ml); WCS120 was expressed and purified as described in this application; WCOR410 was expressed by subcloning the coding region into the vector pET22b. The protein was purified using the His*Bind™ buffer kit protocol described by the company (Novagen).

The different denaturation treatments were as follows: Heat denaturation was achieved by incubating the above enzyme preparations at 60° C. for 10 min; Desiccation was achieved by evaporating the above enzyme preparations to dryness under vacuum (45 min). The enzyme was reconstituted to the original volume before measuring the remaining activity; Cold denaturation was achieved by incubating the above enzyme preparations at −20° C. for 24 hours.

The remaining enzyme activity was determined by incubating 15 μl (4.2 mU) of the different enzyme preparations and the results expressed as a percent of the control value. The reaction (200 μl final volume) was initiated by adding the enzyme to the following: 100 μl of 100 mM $KPO_4$ buffer pH 7.5, 50 μl of 3 mM 5,5'-dithiobis-(2-nitrobenzoic acid) prepared in 10 mM $KPO_4$ pH 7.5, 10 μl of 20 mM oxidized glutathione, 10 μl of 2 mM NADPH, and 15 μl of $H_2O$. The activity was measured spectrophotometrically by following the absorbance at 412 nm.

Results represented in Table I, show that the glutathione reductase is sensitive to the different treatments and can be protected by the addition of purified proteins. BSA is used as a reference since it is a well known protein used to increase enzyme stability under a variety of conditions. Used at 100 and 10 μg/ml, the different proteins appear to give equivalent protection against heat denaturation, desiccation, or cold denaturation. However, used at 1 μg/ml, both WCS120 and WCOR410 are more efficient at protecting against cold denaturation. These in vitro tests suggest that the isolated proteins may play a role as general protectants for enzymes or other cellular structures in vivo. We are now performing transformation experiments to express these and other proteins in transgenic plants in order to evaluate the degree of protection conferred by these proteins against heat, cold and desiccation stresses in vivo.

TABLE I

| Treatments | | 60° C. | Desiccation | −20° C. |
| --- | --- | --- | --- | --- |
| control | | 100% | 100% | 100% |
| GR alone | | 24 | 21 | 4 |
| GR | 100 μg/ml | 66 | 75 | — |
| + | 10 | 57 | 57 | 71 |
| BSA | 1 | 39 | 24 | 13 |
| GR | 100 | 81 | 79 | — |
| + | 10 | 80 | 56 | 80 |
| WCS120 | 1 | 63 | 22 | 40 |
| GR | 100 | — | 81 | — |
| + | 10 | — | 69 | 68 |
| WCOR410 | 1 | — | 23 | 42 |

The genes disclosed in this application are intended to be used in the construction of expression vectors which will produce the encoded proteins, these proteins conferring freezing resistance to host cells, bacteria or plants tissues, or these proteins when extracted being usable as anti-freezing agents.

The production of economic plant species which would be freezing-resistant is particularly envisaged.

REFERENCES

1. Baker J, Steele C, Dure III, L: Sequence and characterization of 6 lea proteins and their genes from cotton. Plant Mol Biol 11: 277–291 (1988).

2. Cadieux C, Sarhan F, Perras M: Osmotic adjustment and photosynthetic electron transport response to cold hardening in winter and spring wheat. Plant Physiol Biochem 26: 313–322 (1988).

3. Cattivelli L, Bartels D: Molecular cloning and characterization of cold-regulated genes in barley. Plant Physiol 93: 1504–1510 (1990).

4. Chevrier N, Qureshi J A. Hucl P, Kartha K K: Heritability of in vitro regeneration in wheat (Triticum aestivum L.). Can J Plant Sci 70: 547–550 (1990).

5. Close T J, Kortt A A, Chandler P M: A cDNA-based comparison of dehydration induced proteins (dehydrins) in barley and corn. Plant Mol Biol 13: 95–108 (1989).

6. Cox W, Levitt J: Interrelation between environmental factors and freezing resistance of cabbage leaves. Plant Physiol 57: 553–555 (1976).

7. Danyluk J, Rassart E, Sarhan F: Gene expression during cold and heat shock in wheat. Biochem Cell Biol 69: 383–391 (1991).

8. Danyluk J, Sarhan, F: Differential mRNA transcription during the induction of freezing tolerance in spring and winter wheat. Plant Cell Physiol 31: 609–619 (1990).

9. Dunn M A, Hughes M A, Pearce R S, Jack P L: Molecular characterization of a barley gene induced by cold treatment. J Exp Bot 41: 1405–1413 (1990).

10. Gagné Y: Rôle de l'acide absicissique lors de l'acclimatation au froid chez le blé MSc. Thesis Université du Québec a Montréal (1991).

11. Garnier J, Osguthorpe D J, Robson B: Analysis of the accuracy and implications of simple methods for predicting the secondary structure of globular proteins. J Mol Biol 120: 97–120 (1978).

12. Goldstein J, Pollitt N S, Inouyé M: Major cold shock protein of Escherichia coli. Proc Natl Acad Sci USA 87: 283–287 (1990).

13. Guy C L: Cold acclimation and freezing stress tolerance: role of protein metabolism. Ann Rev Plant Physiol Plant Mol Biol 41: 187–223 (1990).

14. Houde M, Danyluk J, Laliberté J F, Rassart E, Dhindsa R S, Sarhan F: Cloning, characterization, and expression of a cDNA encoding a 50-kilodalton protein specifically induced by cold acclimation in wheat. Plant Physiol 99: 1381–1387 (1992).

15. Houde M, Dhindsa R S, Sarhan F: A molecular marker to select for freezing tolerance in gramineae. Mol Gen Genet 234: 43–48 (1992).

16. Jacobsen J V, Shaw D C: Heat stable proteins and abscisic acid action in barley aleurone cells. Plant Physiol 91: 1520–1526 (1989).

17. Kurkela S, Franck M: Cloning and characterization of a cold- and ABA-induced Arabidopsis gene. Plant Mol Biol 15: 137–144 (1990).

18. Kyte J, Doolittle R F: A simple method for displaying the hydrophobic character of a protein. J Mol Biol 157: 105–132 (1982).

19. Laemmli U K: Cleavage of structural proteins during the assembly of the head of bacteriophage T4. Nature 227: 680–685 (1970).

20. Lin C, Guo W W, Everson E, Thomashow M F: Cold acclimation in Arabidopsis and wheat. Plant Physiol 94: 1078–1083 (1990).

21. Lin C, Thomashow M: DNA sequence analysis of a complementary DNA for cold regulated Arabidopsis cor15 and characterization of the cor15 polypeptide. Plant Physiol 99: 519–525 (1992).

22. Luo M, Liu J H, Mohapatra S, Hill R D, Mohapatra S S: Characterization of a gene family encoding abscisic acid- and environmental stress-induced proteins of alfalfa. J Biol Chem 267: 15367–15374 (1992).

23. Mermod N, O'neill E A, Kelly T J, Tijian, R: The proline-rich transcriptional activator of CTF/NF-1 is distinct from the replication and DNA binding domain. Cell 58: 741753 (1989).

24. Mohapatra S S, Poole R J, Dhindsa R S: Abscisic acid-regulated gene expression in relation to freezing tolerance in Alfalfa. Plant Physiol 87: 468–473 (1988).

25. Mohapatra S S, Wolfraim L, Poole R J, Dhindsa R S: Molecular cloning and relation to freezing tolerance of cold-acclimation-specific genes of Alfalfa. Plant Physiol 89: 375–380 (1989).

26. Mundy J, Chua N H: Abscisic acid and water stress induce the expression of a novel rice gene. EMBO J 7: 2279–2286 (1988).

27. Murashige T, Skoog F: A reversed medium for rapid growth and bioassays with tobacco tissue cultures. Plant Physiol 15: 473–497 (1962).

28. Nordin K, Heino P, Palva E T: Separate signal pathways regulate the expression of a low-temperature-induced gene in *Arabidopsis thaliana* (L.) Heynh. Plant Mol Biol 16: 1061–1071 (1991).

29. Oquist G, Vaughan M H, Huner N P A: Low-temperature effects on photosynthesis and correlation with freezing tolerance in spring and winter cultivars of wheat and rye. Plant Physiol 101: 245–250 (1993).

30. Ouellet F, Houde M, Sarhan, F: Cloning of the 200 kDa protein induced by cold acclimation in wheat. Plant Cell Physiol 34: 59–65 (1993).

31. Perras M, Sarhan F: Synthesis of freezing tolerance proteins in leaves, crown and roots during cold acclimation of wheat. Plant Physiol 89: 577–585 (1989).

32. Ptashne M: How eukaryotic transcriptional activators work. Natur 335: 683–689 (1988).

33. Rocher-Chambonet C, Berreur P, Houde M, Tiveron M C, Lepesant J A, Brégégére F: Cloning and partial characterization of the xanthine dehydrogenase gene of *Calliphora vicina*, a distant relative of *Drosophila melanogaster*. Gene 59: 201–212 (1987).

34. Rogers S O, Bendich A J: Extraction of DNA from plant tissues. Plant Mol Biol Manual A6: 1–10 (1988).

35. Rosen K M, Villa-Komaroff L: An alternative method for the visualization of RNA in formaldehyde agarose gels. Focus 12: 23–24 (1990).

36. Sambrook J, Fritsch E F, Maniatris T: Molecular cloning: A laboratory manual, 2nd ed. Cold Spring Harbor, New York (1989).

37. Sanger F, Nicklen S, Coulson A R: DNA sequencing with chain-terminating inhibitors. Proc Natl Acad Sci USA 74: 5463–5467 (1977).

38. Sarhan F, Chevrier N: Regulation of RNA synthesis by DNA-dependent RNA polymerase and RNases during cold acclimation in winter and spring wheat. Plant Physiol 78: 250–255 (1985).

39. Siminovitch D, Cloutier Y: Twenty-four hour induction of freezing and drought tolerance in plumules of winter rye seedlings by desiccation stress at room temperature and in the dark. Plant Physiol 69: 250–255 (1982).

40. Steponkus P L, Lynch D V: Freeze/thaw-induced destablization of the plasma membrane and the effects of cold-acclimation. J Bioenerg Biomembr 21: 21–41 (1989).

41. Tabata T, Takase H, Takayama S, Mikami K, Nakatsuka A, Kawata T, Nakayama T, Iwabuchi M: A protein that binds to a cis-acting element of wheat histone gene has a leucine zipper motif. Science 245: 965–967 (1989).

42. Thomashow M F: Molecular genetics of cold acclimation in higher plants. Adv Genet 28: 99–31 (1990).

43. Vilardell J, Goday A, Freire M A, Torrent M, Martinez M C, Torné J M, Pages M: Gene sequence, developmental expression, and protein phosphorylation of Rab-17 in maize. Plant Mol Biol 14: 423–432 (1990).

44. Weisshaar B, Armstrong G A, Block A, Oswaldo C S, Hahlbrock K: Light inducible and constitutively expressed DNA-binding proteins recognizing a plant promoter element with functional relevance in light responsiveness. EMBO J 10: 1777–1786 (1991).

45. Weretilnyk E A, Hanson A D: Molecular cloning of a plant betaine-aldehyde dehydrogenase, an enzyme implicated in adaptation to salinity and drought. Proc Natl Acad Sci USA 87: 2745–2749 (1990).

46. Weretilnyk E, Winson O, White T C, lu B, Singh J: Characterization of three related low-temperature-regulated cDNAs from winter *Brassica Napus*. Plant Physiol 101: 171–177 (1993).

47. Yamaguchi-Shinozaki K, Mundy J, Chua N-H: Four tightly linked rab genes are differentially expressed in rice. Plant Mol Biol 14: 29–39 (1989).

48. Yanish-Perron C, Vieira J, Messing J: Improved M13 phage cloning vectors and host strains: nucleotide sequences of M13mp18 and pUC19 vectors. Gene 33: 103–119 (1985).

49. Zachariassen K E: Physiology of cold tolerance in insects. Physiol Rev 65: 799–832 (1985).

50. Guo W, Ward R W, Thomashow M F: Characterization of a Cold-Regulated Wheat Gene Related to Arabidopsis cor47. Plant Physiol. 915–922 (1992).

We claim:

1. An isolated protein, named Wcs19, having the amino acid sequence as shown in SEQ ID NO:2.

2. An isolated protein, named Wcor410, having the amino acid sequence as shown in SEQ ID NO:6.

* * * * *

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 943
        ( B ) TYPE: Nucleic acid
        ( C ) STRANDEDNESS: Double
        ( D ) TOPOLOGY: Linear ( i i ) MOLECULE TYPE: cDNA to mRNA ( v i ) ORIGINAL SOURCE: Triticum Aestivum L.

( x i ) SEQUENCE DESCRIPTION: SEQ ID NO: 1:

```
TTTTTTTTTG   CGACCAAAAT   GAACAAGTAA   ATTTACTCCC   TCACAAGCAT        50
ATGCAAATAT   ATTCCACCAA   GAATATTAGT   CGGTCCTCGC   TATCAACCAC       100
ATCTAAAACC   ATGTCAACGA   ATGGAAACAA   CACCACCTTA   AAAGTATCCA       150
CACGAGAAGG   CTCCTTATAT   TTGTATTAAC   AGAAGAGCAA   AAAGATATAG       200
CTGTATGATT   TCAGCGATCC   AAATCCGCAT   GGTGCAGCGA   TGCGCAAGAC       250
TACCATTTCC   AATCGGCACA   CATCCTGTCT   CCTTCCACAA   CCTACCCTAC       300
CCACCCATCC   ATCAGCAGTT   TTTCTATCGA   CCAATGGCTT   CTTCTTCCGT       350
GCTGCTCGGA   GCCTCGGCCA   CGGCCGCGCT   CACCGGCACC   CCGGCAGGCA       400
AGGCCCTTCC   CCGGCCTTGC   TTCCTCGCCG   CTCGCCCGCG   CACCGTGAGC       450
GGTGGCCGTC   TCTGCCTGCA   GAACGCTCCA   AGGGCGACTC   CGGCGTACAA       500
CGACGCTGCG   GATGCCACCG   ACAAGGCCAT   CGACGGCGTG   AAGGGGGTGG       550
CCGACGAGTT   GAAGAAGGGC   GTGGCGGAGG   CTGCGGAGGC   CGTCTCGGGC       600
AACACCGAGA   AGGCCGCGGA   GGAAGCCGGC   AAGGGCGCGA   GCGAGGTGGA       650
CGCGAAGGCC   AAGGACTTCG   GCGAGCAGGC   GAAGAAGGCG   ACGGAGGAGG       700
CGTGGGACGG   CGCCAAGGAC   GCCGCACAGG   GCATCACGGA   CAAAGTCGCC       750
GCCGCGGCCA   AAAAGGAAGC   TAGCTAAGCT   AACACTACGT   TGACTAGTCC       800
GATCTGTATC   GCTCAATTCA   TTTTCCATTG   TAAGGAATGC   ATATACGTAT       850
TTCGGTACAA   GAGATAAGAT   AGCTGTATTT   ATTTTCTGTG   ATATAGGATT       900
ACCGCACTGT   TAATGTCAAA   CGCAATAAAG   AAAATGATTT   TTY              943
```

( 2 ) INFORMATION FOR SEQ ID NO: 2:

( i ) SEQUENCE CHARACTERISTICS:
       ( A ) LENGTH: 190
       ( B ) TYPE: Amino acid
       ( D ) TOPOLOGY: Unknown ( i i ) MOLECULE TYPE: Protein ( v i ) ORIGINAL SOURCE: Triticum Aestivum L.

( x i ) SEQUENCE DESCRIPTION: SEQ ID NO: 2:

```
Met  Ile  Ser  Ala  Ile  Gln  Ile  Arg  Met  Val
                    5                        10

Gln  Arg  Cys  Ala  Arg  Leu  Pro  Phe  Pro  Ile
                   15                        20

Gly  Thr  His  Pro  Val  Ser  Phe  His  Asn  Leu
                   25                        30

Pro  Tyr  Pro  Pro  Thr  His  Gln  Gln  Phe  Phe
                   35                        40

Tyr  Arg  Pro  Met  Ala  Ser  Ser  Ser  Val  Leu
                   45                        50

Leu  Gly  Ala  Ser  Ala  Thr  Ala  Ala  Leu  Thr
                   55                        60

Gly  Thr  Pro  Ala  Gly  Lys  Ala  Leu  Pro  Arg
                   65                        70

Pro  Cys  Phe  Leu  Ala  Ala  Arg  Pro  Arg  Thr
                   75                        80

Val  Ser  Gly  Gly  Arg  Leu  Cys  Leu  Gln  Asn
                   85                        90
```

| | | | | | | | | | |
|---|---|---|---|---|---|---|---|---|---|
| Ala | Pro | Arg | Ala | Thr<br>95 | Pro | Ala | Tyr | Asn | Asp<br>100 |
| Ala | Ala | Asp | Ala | Thr<br>105 | Asp | Lys | Ala | Ile | Asp<br>110 |
| Gly | Val | Lys | Gly | Val<br>115 | Ala | Asp | Glu | Leu | Lys<br>120 |
| Lys | Gly | Val | Ala | Glu<br>125 | Ala | Ala | Glu | Ala | Val<br>130 |
| Ser | Gly | Asn | Thr | Glu<br>135 | Lys | Ala | Ala | Glu | Glu<br>140 |
| Ala | Gly | Lys | Gly | Ala<br>145 | Ser | Glu | Val | Asp | Ala<br>150 |
| Lys | Ala | Lys | Asp | Phe<br>155 | Gly | Glu | Gln | Ala | Lys<br>160 |
| Lys | Ala | Thr | Glu | Glu<br>165 | Ala | Trp | Asp | Gly | Ala<br>170 |
| Lys | Asp | Ala | Ala | Gln<br>175 | Gly | Ile | Thr | Asp | Lys<br>180 |
| Val | Ala | Ala | Ala | Ala<br>185 | Lys | Lys | Glu | Ala | Ser<br>190 |

( 2 ) INFORMATION FOR SEQ ID NO: 3:

( i ) SEQUENCE CHARACTERISTICS:
        ( A ) LENGTH: 1522
        ( B ) TYPE: Nucleic acid
        ( C ) STRANDEDNESS: Double
        ( D ) TOPOLOGY: Linear ( i i ) MOLECULE TYPE: cDNA to mRNA ( v i ) ORIGINAL SOURCE: Triticum Aestivum L.

( x i ) SEQUENCE DESCRIPTION: SEQ ID NO: 3:

```
CGAGTGAGGA  GCTCAGCGCA  AGATGGAGAA  CCAGGCACAC  ATCGCCGGCG        50
AGAAGAAGGG  CATCATGGAG  AAGATCAAGG  AGAAGCTCCC  CGGCGGCCAC       100
GGCGACCACA  AGGAGACCGC  TGGTACCCAC  GGGCACCCCG  GCACGGCGAC       150
GCATGGTGCC  CCGGCCACTG  GTGGTGCCTA  CGGGCAGCAG  GGTCACGCTG       200
GAACCACCGG  CACGGGGTTG  CATGGCGCCC  ACGCCGGCGA  GAAGAAGGGC       250
GTCATGGAGA  ACATCAAGGA  CAAGCTCCCT  GGTGGCCACC  AGGACCACCA       300
GCAGACTGGT  GGTACCTATG  GGCAGCAGGG  ACACACCGGC  ACGGCGACGC       350
ATGGCACCCC  GGCGACCGGT  GGCACCTATG  GGCAGCAGGG  ACATACCGGC       400
ACAGCGACGC  ATGGCACCCC  GGCGACCGGT  GGCACCTATG  GGGAGCAGGG       450
ACACACCGGA  GTGACTGGCA  CGGGGACGCA  CGGCACCGGC  GAGAAGAAGG       500
CGGTGACCAC  GAACATCAAG  GAGAAGCTCC  CTGGTGGCCA  CGGCACCGGC       550
CAGCAGACCG  GTGGTACCTA  CGGGCAGCAG  GGACACACCG  GCACGGCGAC       600
GCATGGCACC  CCGGCCGGGG  GCGGCACCTA  TGAGCAGCAC  GGACACACCG       650
GGATGACCGG  CACAGGGACA  CACGGCACTG  GCGAGAAGAA  AGGCGTCATG       700
GAGAACATCA  AGGACAAGCT  CCCTGGTGGC  CACGGAGATC  ACCAGCAGAC       750
CGGTGGCACC  TACGGGCAGC  AGGGACACAC  CGGCACGGCG  ACACAGGGCA       800
CCCCGGCCGG  CGGCGGCACC  TATGAGCAGC  ATGGACACAC  CGGGATGACC       850
GGCGCGGGGA  CACACAGCAC  TGGCGAGAAG  AAGGGCGTCA  TGGAGAACAT       900
```

```
CAAGGAAAAG CTCCCTGGTG GCCACAGTGA CCACCAGCAG ACCGGTGGAG        950

CCTACGGGCA GCAGGGACAC ACCGGCACGC GACACATGGC ACCCCTGCCG       1000

GCGGGCACCT ACGGGCAGCA TGGACACGCT GGAGTGATCG GCACGGAGAC       1050

GCATGGCACC ACGGCCACCG GCGGCACCCA TGGGCAGCAC GGACACACCG       1100

GAACGACTGG CACTGGGACA CACGGCTCCG ACGGGATCGG CGAGAAGAAG       1150

AGCCTCATGG ACAAGATCAA GGATAAGCTG CCTGGACAGC ACTGAGCCCG       1200

GTCTGCCCGC GGCCGCTACC CTTGCAGAAT AATAACCCCA CCGTGTATAA       1250

GTTAATTGAG TCTAGTTCAC CTAGCTCACT TGGTCGTTGG AGGAGAGAAT       1300

GTATTATGTA TCTTGGTTTA AGTTTCACG GACAACAGTG TGTTCACAGT        1350

TTTCTTCTGT TTACACTCTG TAGTGCAAAT TCGTTTAAGT TTTCACGGAC       1400

AACAGTGTGT TCACAGTTTT CTTCTGTTTA CACTCTGTAG TGCAAATTTC       1450

GTTTTGTTC TTTTTTTTT TGTCCATCTT ATCCAAGAGA CAGACGCAGC         1500

GAAAAAAAAA AAAAAAAAA AA                                      1522
```

( 2 ) INFORMATION FOR SEQ ID NO: 4:

( i ) SEQUENCE CHARACTERISTICS:
        ( A ) LENGTH: 390
        ( B ) TYPE: Amino acid
        ( D ) TOPOLOGY: Unknown ( i i ) MOLECULE TYPE: Protein ( v i ) ORIGINAL SOURCE: Triticum Aestivum L.

( x i ) SEQUENCE DESCRIPTION: SEQ ID NO: 4:

```
Met Glu Asn Gln Ala His Ile Ala Gly Glu
                  5                   10

Lys Lys Gly Ile Met Glu Lys Ile Lys Glu
                 15                   20

Lys Leu Pro Gly Gly His Gly Asp His Lys
                 25                   30

Glu Thr Ala Gly Thr His Gly His Pro Gly
                 35                   40

Thr Ala Thr His Gly Ala Pro Ala Thr Gly
                 45                   50

Gly Ala Tyr Gly Gln Gln Gly His Ala Gly
                 55                   60

Thr Thr Gly Thr Gly Leu His Gly Ala His
                 65                   70

Ala Gly Glu Lys Lys Gly Val Met Glu Asn
                 75                   80

Ile Lys Asp Lys Leu Pro Gly Gly His Gln
                 85                   90

Asp His Gln Gln Thr Gly Gly Thr Tyr Gly
                 95                  100

Gln Gln Gly Thr His Gly Thr Ala Thr His
                105                  110

Gly Thr Pro Ala Thr Gly Gly Thr Tyr Gly
                115                  120

Gln Gln Gly His Thr Gly Thr Ala Thr His
                125                  130
```

-continued

```
Gly Thr Pro Ala Thr Gly Gly Thr Tyr Gly
                135                     140

Glu Gln Gly His Thr Gly Val Thr Gly Thr
                145                     150

Gly Thr His Gly Thr Gly Glu Lys Lys Gly
                155                     160

Val Met Glu Asn Ile Lys Glu Lys Leu Pro
                165                     170

Gly Gly His Gly Asp His Gln Gln Thr Gly
                175                     180

Gly Thr Tyr Gly Gln Gln Gly His Thr Gly
                185                     190

Thr Ala Thr His Gly Thr Pro Ala Gly Gly
                195                     200

Gly Thr Tyr Glu Gln His Gly His Thr Gly
                205                     210

Met Thr Gly Thr Gly Thr His Gly Thr Gly
                215                     220

Glu Lys Lys Gly Val Met Glu Asn Ile Lys
                225                     230

Asp Lys Leu Pro Gly Gly His Gly Asp His
                235                     240

Gln Gln Thr Gly Gly Thr Tyr Gly Gln Gln
                245                     250

Gly His Thr Gly Thr Ala Thr Gln Gly Thr
                255                     260

Pro Ala Gly Gly Gly Thr Tyr Glu Gln His
                265                     270

Gly His Thr Gly Met Thr Gly Ala Gly Thr
                275                     280

His Ser Thr Gly Glu Lys Lys Gly Val Met
                285                     290

Glu Asn Ile Lys Glu Lys Leu Pro Gly Gly
                295                     300

His Ser Asp His Gln Gln Thr Gly Gly Ala
                305                     310

Tyr Gly Gln Gln Gly His Thr Gly Thr Arg
                315                     320

His Met Ala Pro Leu Pro Ala Gly Thr Tyr
                325                     330

Gly Gln His Gly His Ala Gly Val Ile Gly
                335                     340

Thr Glu Thr His Gly Thr Thr Ala Thr Gly
                345                     350

Gly Thr His Gly Gln His Gly His Thr Gly
                355                     360

Thr Thr Gly Thr Gly Thr His Gly Ser Asp
                365                     370

Gly Ile Gly Glu Lys Lys Ser Leu Met Asp
                375                     380

Lys Ile Lys Asp Lys Leu Pro Gly Gln His
                385                     390
```

( 2 ) INFORMATION FOR SEQ ID NO: 5:

(i) SEQUENCE CHARACTERISTICS:
    (A) LENGTH: 1136
    (B) TYPE: Nucleic acid
    (C) STRANDEDNESS: Double
    (D) TOPOLOGY: Linear (ii) MOLECULE TYPE: cDNA to mRNA (vi) ORIGINAL SOURCE: Triticum Aestivum L.

(xi) SEQUENCE DESCRIPTION: SEQ ID NO: 5:

| | | | | | |
|---|---|---|---|---|---|
| AAAAGCCACA | AGCCAAGAAC | CAATACTTGA | TCTGTTGTTT | CCTTTAGCTC | 50 |
| CCGGAAGACT | TTTAGCTGCA | CCGATCGATC | TCGATCATGG | AGGATGAGAG | 100 |
| GAGCACCCAG | TCGTACCAGG | GAGGTGAGGC | CGCCGAGCAG | GTGGAGGTGA | 150 |
| CGGACAGGGG | CCTCCTCGGC | AACCTCCTCG | GCAAGAAGAA | GGCTGAGGAG | 200 |
| GACAAGGAGA | AGGAGGAGGA | GCTGGTCACC | GGCATGGAGA | AGGTCTCCGT | 250 |
| GGAAGAGCCC | GAGGTCAAGA | AGGAGGAGCA | CGAGGATGGC | GAGAAGAAGG | 300 |
| AGACCCTCTT | CTCCAAGCTG | CACCGATCCA | GCTCCAGCTC | CAGCTCGTCT | 350 |
| AGTGACGAGG | AAGAAGAGGA | GGTGATCGAT | GACAACGGCG | AGGTGATCAA | 400 |
| GAGGAAGAAG | AAGAAGGGGC | TCAAGGAAAA | GCTCCAGGGG | AAGCTGCCCG | 450 |
| GCCACAAGGA | CACCGAGGGT | GAGCACGTGA | CGGGGCTACC | GGCACCGGCG | 500 |
| GCCCCCGCGT | CTGTGCAGAC | CCACGGCGGC | CACCATGACA | CCGACGTCGT | 550 |
| CGTCGAGAAG | ATCGACGGCG | ACGTGAAGAC | AGAGGCGGCA | CCGGCAGTGC | 600 |
| CCGAGGAGGA | GAAGAAAGGC | TTCTTGGAAA | AGATCAAGGA | GAAGCTGCCC | 650 |
| GGCGGCCACA | AGAAGCCGGA | GGACGCTGCT | GCGGTGCCCG | TCACGCACGC | 700 |
| TGCTCCAGCA | CCAGTGCACG | CGCCGGTGCC | GGCCCCCGAG | GAGGTGAGCA | 750 |
| GCCCTGACGC | GAAGGAGAAG | AAGGGCCTGC | TGGGCAAGAT | CATGGACAAG | 800 |
| CTGCCTGGTT | ACCACAAGAC | AGGGGAGGAG | GACAAGGCCG | CCGCCGCTAC | 850 |
| AGGCGAGCAC | AAGCCCAGCG | CTTGATCGCC | GCCGTGCCCG | AGACCCGTGA | 900 |
| CCGGACCTCG | ATTGAATTGT | TGGCGTGTGT | TGTGTTTGCT | TTACGTCTAA | 950 |
| GTTGGTGTCA | AGGTGGGAGG | GGTTGATCGT | CTTTGAAGGT | CCGGTCCGTG | 1000 |
| AAGCCCGTTC | AGTGACGGGT | GCTTCTGTTT | CAGTTTGGTT | CAGAGTCAGG | 1050 |
| TCCTGGATGT | TGTCAAGTTT | GTTACTTAT | GGGCACTTGT | GTATTGGTTT | 1100 |
| ATTGCTGGGC | ATTATGCCTT | GATATTAAAG | ATTTCC | | 1136 |

(2) INFORMATION FOR SEQ ID NO: 6:

(i) SEQUENCE CHARACTERISTICS:
        (A) LENGTH: 262
        (B) TYPE: Amino acid
        (D) TOPOLOGY: Unknown (ii) MOLECULE TYPE: Protein (vi) ORIGINAL SOURCE: Triticum Aestivum L.

(xi) SEQUENCE DESCRIPTION: SEQ ID NO: 6:

| Met | Glu | Asp | Glu | Arg | Ser | Thr | Gln | Ser | Tyr |
|---|---|---|---|---|---|---|---|---|---|
| | | | | 5 | | | | | 10 |
| Gln | Gly | Gly | Glu | Ala | Ala | Glu | Gln | Val | Glu |
| | | | | 15 | | | | | 20 |
| Val | Thr | Asp | Arg | Gly | Leu | Leu | Gly | Asn | Leu |

```
                            25                              30
Leu Gly Lys Lys Lys Ala Glu Glu Asp Lys
                    35                              40
Glu Lys Glu Glu Glu Leu Val Thr Gly Met
                    45                              50
Glu Lys Val Ser Val Glu Glu Pro Glu Val
                    55                              60
Lys Lys Glu Glu His Glu Asp Gly Glu Lys
                    65                              70
Lys Glu Thr Leu Phe Ser Lys Leu His Arg
                    75                              80
Ser Ser Ser Ser Ser Ser Ser Ser Ser Asp
                    85                              90
Glu Glu Glu Glu Glu Val Ile Asp Asp Asn
                    95                              100
Gly Glu Val Ile Lys Arg Lys Lys Lys Lys
                    105                             110
Gly Leu Lys Glu Lys Leu Gln Gly Lys Leu
                    115                             120
Pro Gly His Lys Asp Thr Glu Gly Glu His
                    125                             130
Val Thr Gly Leu Pro Ala Pro Ala Ala Pro
                    135                             140
Ala Ser Val Gln Thr His Gly Gly His His
                    145                             150
Asp Thr Asp Val Val Val Glu Lys Ile Asp
                    155                             160
Gly Asp Val Lys Thr Glu Ala Ala Pro Ala
                    165                             170
Val Pro Glu Glu Glu Lys Lys Gly Phe Leu
                    175                             180
Glu Lys Ile Lys Glu Lys Leu Pro Gly Gly
                    185                             190
His Lys Lys Pro Glu Asp Ala Ala Ala Val
                    195                             200
Pro Val Thr His Ala Ala Pro Ala Pro Val
                    205                             210
His Ala Pro Val Pro Ala Pro Glu Glu Val
                    215                             220
Ser Ser Pro Asp Ala Lys Glu Lys Lys Gly
                    225                             230
Leu Leu Gly Lys Ile Met Asp Lys Leu Pro
                    235                             240
Gly Tyr His Lys Thr Gly Glu Glu Asp Lys
                    245                             250
Ala Ala Ala Ala Thr Gly Glu His Lys Pro
                    255                             260
Ser Ala
```

( 2 ) INFORMATION FOR SEQ ID NO:7:

( i ) SEQUENCE CHARACTERISTICS:
    ( A ) LENGTH: 29 base pairs
    ( B ) TYPE: nucleic acid
    ( C ) STRANDEDNESS: single ( D ) TOPOLOGY: linear ( i i ) MOLECULE TYPE: DNA (genomic)

( x i ) SEQUENCE DESCRIPTION: SEQ ID NO:7:

AGTGAGGATC CCAGCGCCAT ATGGAGAAC     29

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GTTGTCCGGT GGATCCTTAA AC     22

( 2 ) INFORMATION FOR SEQ ID NO:9:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

Gly Glu Lys Lys Gly Val Met Glu Asn Ile Lys Glu Lys Leu Pro Gly
1               5                   10                  15

Gly His Gly Asp His Gln Gln
                20

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

Thr Gly Gly Thr Tyr Gly Gln Gln Gly His Thr Gly Thr Thr
1               5                   10

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

Ser Gly Ser Ser Ser Ser Ser Ser Ser
1               5